US006342345B1

(12) United States Patent
Blau et al.

(10) Patent No.: US 6,342,345 B1
(45) Date of Patent: Jan. 29, 2002

(54) DETECTION OF MOLECULAR INTERACTIONS BY REPORTER SUBUNIT COMPLEMENTATION

(75) Inventors: Helen M. Blau, Menlo Park; Fabio Rossi, Atherton, both of CA (US); William Mohler, Madison, WI (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 09/053,614

(22) Filed: Apr. 1, 1998

Related U.S. Application Data
(60) Provisional application No. 60/042,576, filed on Apr. 2, 1997, and provisional application No. 60/054,638, filed on Aug. 4, 1997.

(51) Int. Cl.[7] .............................. C12Q 1/00; C12Q 1/68; C12N 5/10; C12N 15/11; C12N 15/63
(52) U.S. Cl. ........................... 435/4; 435/6; 435/320.1; 435/325; 530/350; 536/23.2; 536/23.4; 536/23.5; 536/23.7
(58) Field of Search ............................. 435/4, 6, 320.1, 435/325; 530/350; 536/23.2, 23.4, 23.5, 23.7

(56) References Cited

U.S. PATENT DOCUMENTS

| 4,708,929 | A | | 11/1987 | Henderson |
| 5,223,393 | A | * | 6/1993 | Khanna et al. ................. 435/6 |
| 5,362,625 | A | | 11/1994 | Krevolin et al. |
| 5,503,977 | A | | 4/1996 | Johnsson et al. |
| 5,585,245 | A | | 12/1996 | Johnsson et al. |

FOREIGN PATENT DOCUMENTS

| CA | 2196496 | 7/1998 |
| EP | 0 601 889 A2 | 6/1994 |
| WO | WO 95/07463 | 3/1995 |
| WO | WO 96/23810 | 8/1996 |
| WO | WO 96/30540 | 10/1996 |
| WO | WO 96/41166 | 12/1996 |
| WO | WO 98/34120 | 8/1998 |

OTHER PUBLICATIONS

Johnsson et al. Split ubiquitin as a swnsor of protein interactions in vivo. Proc. Natl. Acad. Sci. USA vol. 91 pp. 10340–10344, 1994.*
Yan et al., "Differential ability to form the G protein βγ complex among members of the β and γ subunit families" *J. Biol Chem.* (1996) 271:7141–7146.
Adams et al., "Fluorescence ratio imaging of cyclic AMP in single cells" (1991) *Nature* 349: 694–697.
Alberti et al., "A single laser method for subtraction of cell autofluorescence in flow cytometry" (1987) *Cytometry* 8:114–119.

Bai et al., "Gene identification using the yeast two–hybrid system" (1996) *Meth. Enzymol.* 273:331–347.
Beckwith, J.R., "A deletion analysis of the Lac operator region in *Escherichia coli*" (1964) *J. Mol. Biol.* 8:427–430.
Beerli et al., "Epidermal growth factor–related peptides activate distinct subsets of ErbB receptors and differ in their biological activities" (1996) *J. Biol. Chem.* 271:6071–6076.
Belshaw et al., "Controlling protein association and subcellular localization with a synthetic ligand that induces heterodimerization of proteins" (1996) *Proc. Natl. Acad. Sci. USA* 93: 4604–4607.
Benezra et al., "The protein Id: A negative regulator of helix–loop–helix DNA binding proteins" (1990) *Cell* 61:49–59.
Bronstein et al. "1,2–dioxetanes: Novel chemiluminescent enzyme substrates. Applications to immunoassays" (1989) *J. Biolumin. Chemilumin.* 4:99–111.
Brown et al., "A mammalian protein targeted by G1–arresting rapamycin–receptor complex" (1994) *Nature* 369: 756–758.
Capecchi, M.R., "Altering the genome by homologous recombination" (1989) *Science* 244: 1288–1292.
Chen, Z–F., "Twist is required in head mesenchyme for cranial neural tube morphogenesis" (1995) *Genes Devel.* 9:686–699.
Chen et al., "I–mf, a novel myogenic repressor, interacts with members of the MyoD family" (1996) *Cell* 86:731–741.
Chen et al., "Identification of an 11–kDa FKBP12–rapamycin–binding domain within the 289–kDaFKBP12–rapamycin–associated protein and characterization of a critical serine residue" (1995) *Proc. Natl. Acad. Sci. USA* 92:4947–4951.
Choi et al., "Structure of the FKBP12–rapamycin complex interacting with the binding domain of human FRAP" (1996) *Science* 273:239–242.

(List continued on next page.)

*Primary Examiner*—John S. Brusca
(74) *Attorney, Agent, or Firm*—Morrison & Foerster LLP

(57) ABSTRACT

Methods and compositions for detecting molecular interactions, particularly protein-protein interactions, are provided. The invention allows detection of such interactions in living cells or in vitro. Detection of molecular interactions in living cells is not limited to the nuclear compartment, but can be accomplished in the cytoplasm, cell surface, organelles, or between these entities. In one embodiment, the method utilizes novel compositions comprising fusion proteins between the molecules of interest and two or more inactive, weakly-complementing β-galactosidase mutants. Association between the molecules of interest brings the complementing β-galactosidase mutants into proximity so that complementation occurs and active β-galactosidase is produced. The active β-galactosidase may be detected by methods well-known in the art. Among the uses of the invention are the study of protein-protein interactions, functional genomics, agonist and antagonist screening and drug discovery.

111 Claims, 10 Drawing Sheets

OTHER PUBLICATIONS

Cossu et al. "How is myogenesis initiated in the embryo?" (1996) *Trends Genet.* 12:218–223.

Dhawan et al., "Systemic delivery of human growth hormone by injection of genetically engineered myoblasts" (1991) *Science* 254:1509–1512.

Felder et al. "Kinetics of binding, endocytosis, and recycling of EGF receptor mutants" (1992) *J. Cell. Biol.* 117:203–212.

Fields et al., "A novel genetic system to detect protein–protein interactions"(1989) *Nature* 340:245–246.

Fiering et al. "Improved FACS–Gal: Flow cytometric analysis and sorting of viable eukaryotic cells expressing reporter gene constructs" (1991) *Cytometry* 12:291–301.

Fiering et al., "Targeted delection of 5'HS2 of the murine β–globin LCR reveals that it is not essential for proper regulation of the β–globin locus" (1995) *Genes Dev.* 9:2203–2213.

Füchtbauer, E–M., "Expression of M–twist during postimplantation development of the mouse" (1995) *Dev. Dyn.* 204:316–322.

Gadella, Jr. et al., "Oligomerization of epidermal growth factor receptors on A431 cells studied by time–resolved fluorescence imaging microscopy. A stereochemical model for tyrosine kinase receptor activation" (1995) *J. Cell Biol.* 129:1543–1558.

Hebrok et al., "M–twist is an inhibitor of muscle differentiation" (1994) *Dev. Biol.* 165:537–544. (1994).

Hinrichs et al., "Structure of the Tet repressor–tetracycline complex and regulation of antibiotic resistance" (1994) *Science* 264:418–420.

Ho, S. N. et al., "Dimeric ligands define a role for transcriptional activation domains in reinitiation" (1996) *Nature* 382:822–826.

Hu et al., "HEB, a helix–loop–helix protein related to E2A and ITF2 that can modulate the DNA–binding ability of myogenic regulator factors" (1992) *Mol. Cell. Biol.* 12:1031–1042.

Hughes et al., "Migration of myoblasts across basal lamina during skeletal muscle development" (1990) *Nature* 345:350–353.

Jackson et al. "Restoration of enzymic activity by complementation in vitro between mutant αsubunits of tryptophan synthetase and between mutant subunits and fragments of the α subunit" (1969) *J. Biol. Chem.* 244:4539–4546.

Jacobson et al., "Three–dimensional structure of β–galactosidase from *E. coli*" (1994) *Nature* 369:761–766.

Kitamura et al., "Efficient screening of retroviral cDNA expression libraries" (1995) *Proc. Natl. Acad. Sci. USA* 92:9146–9150.

Kiyokawa et al., "Mitosis–specific negative regulation of epidermal growth factor receptor, triggered by a decrease in ligand binding and dimerization, can be overcome by overexpression of receptor" (1997) *J. Biol. Chem.* 272:18656–18665.

Lassar et al., "Functional activity of myogenic HLH proteins requires hetero–oligomerization with E12/E47–like proteins in vivo" (1991) *Cell* 66:305–315.

Levitzki et al., "Tyrosine kinase inhibition: An approach to drug development" (1995) *Science* 267:1782–1788.

Livneh et al., "Reconstitution of human epidermal growth factor receptors and its deletion mutants in cultured hamster cells" (1986) *J. Biol. Chem.* 261:12490–12497.

Luo et al., "Mammalian two–hybrid system: A complementary approach to the yeast tow–hybrid system" (1997) *BioTechniques* 22:350–352.

Minden, J.S., "Synthesis of a new substrate for detecting of lacZ gene expression in live Drosophila embryos" (1996) *BioTechniques* 20:122–129.

Miyawaki et al., "Fluorescent indicators for $Ca^{2+}$ based on green fluorescent proteins and calmodulin" (1997) *Nature* 388:882–887.

Mohler et al., "Gene expression and cell fusion analyzed by lacZ complementation in mammalian cells" (1996) *Proc. Natl. Acad. Sci. USA* 93:12423–12427.

Molkentin et al., "Mutational analysis of the DNA binding, dimerization, and transcriptional activation domains of MEF2C" (1996) *Mol. Cell. Biol.* 16:2627–2636.

Murre et al. "A new DNA binding and dimerization motif in immunoglobulin enhancer binding, daughterless, MyoD, and myc proteins" (1989) *Cell* 56:777–783.

Nolan et al., "Fluorescence–activated cell analysis and sorting of viable mammalian cells based on β–D–galactosidase activity after transduction of *Escherichia coli lacZ*" (1988) *Proc. Natl. Acad. Sci. USA* 85:2603–2607.

Olson et al., "Know your neighbors: Three phenotypes in null mutants of the myogenic bHLH gene MRF4" (1996) *Cell* 85:1–4.

Ott et al., "Early expression of the myogenic regulatory gene, myf–5, in precursor cells of skeletal muscle in the mouse embryo" (1991) *Development* 111: 1097–1107.

Parks et al, "Flow cytometry and fluorescence activated cell sorting (FACS)" (1986) *The Handbook of Experimental Immunology*, (eds. Weir, D.M., Herzenberg, L.A., Blackwell, C.C. & Herzenberg, L.A.), Blackwell, Endinburgh, 4th edition, pp. 29.1–29.21.

Pear et al., "Production of high–titer helper–free retroviruses by transient transfection" (1993) *Proc. Natl. Acad. Sci. USA* 90:8392–8396.

Pookanjanatavip et al., "Subunit complementation of thymidylate synthase" (1992) *Biochemistry* 31:10303–10309.

Prentki, P., "Nucleotide sequence of the classical lacZ deletion ΔM15" (1992) *Gene* 122:231–232.

Rastinejad et al., "Genetic complementation reveals a novel regulatory role for 3' untranslated regions in growth and differentiation" (1993) *Cell* 72:903–917.

Rohwedel et al., "M–twist expression inhibits mouse embryonic stem cell–derived myogenic differentiation in vitro" (1995) *Exp. Cell Res.*, 220:92–100.

Rossi et al., "Monitoring protein–protein interactions in intact eukaryotic cells by β–galactosidase complementation" (1997) *Proc. Natl. Acad. Sci. USA* 94:8405–8410.

Rotman et al., "Fluorogenic substrates for β–D–galactosidases and phosphatases derived from fluorescein (3,6–dihydroxyfluoran) and its monomethyl ether" (1963) *Proc. Natl. Acad. Sci. USA* 50:1–6.

Rudnicki et al., "Inactivation of MyoD in mice leads to up–regulation of the myogenic HLH gene Myf–5 and results in apparently normal muscle development" (1992) *Cell* 71:383–390.

Schlessinger et al., "Growth factor signaling by receptor tyrosine kinases" (1992) *Neuron* 9:383–391.

Smith et al., "Somite subdomains, muscle cell origins, and the four muscle regulatory factor proteins" (1994) *J. Cell Biol.*, 127:95–105.

Spicer et al., "Inhibition of myogenic bHLH and MEF2 transcription factors by the bHLH protein twist" (1996) *Science*, 272:1476–1480.

Stoetzel et al., "Dorso–ventral and rostro–caudal sequential expression of M–twist in the postimplantation murine embryo" (1995) *Mech. Dev. 51*:251–263.

Tajbakhsh et al., "Mouse limb muscle is determined in the absence of the earliest myogenic factor myf–5" (1994) *Proc. Natl. Acad. Sci.* USA, 91:747–751.

Tajbakhsh et al., "Muscle progenitor cells failing to respond to positional cues adopt non–myogenic fates in myf–5 null mice" (1996) *Nature 384*:266–270.

Tajbakhsh et al., "A population of myogenic cells derived from the mouse neural tube" (1994) *Neuron 13*:813–821.

Thomas et al., "Introduction of homologous DNA sequences into mammalian cells induces mutations in the cognate gene" (1986) *Nature 324*:34–38.

Ullman et al., "Identification par Complémentation in vitro et Purification d'un Segment de la β–Galactosidase d'*Escherichia coli*" (1965) *J. Mol. Biol. 12*:918–923.

Ullman et al., "Characterization by in vitro complementation of a peptide corresponding to an operator–proximal segment of the β–galactosidase structural gene of *Escherichia coli*" (1967) *J. Mol. Biol. 24*:339–343.

Ullman et al., "On the subunit structure of wild–type versus complemented β–galactosidase of *Escherichia coli*"(1968) *J. Mol. Biol. 32*:1–13.

Ullrich et al, "Signal transduction by receptors with tyrosine kinase activity" (1990) *Cell 61*:203–212.

Webster et al., "Isolation of human myoblasts with the fluorescence–activated cell sorter" (1988) *Exp. Cell Research*, 174:252–265.

Weiss et al., "Novel mechanisms of RTK signal generation" (1997) *Curr. Opin. Genet. Dev. 7*:80–86.

Yarden et al., "Epidermal growth factor induces rapid, reversible aggregation of the purified epidermal growth factor receptor" (1987) *Biochemistry 26*:1443–1451.

Yun et al., "Skeletal muscle determination and differentiation: story of a core regulatory network and its context" (1996) *Curr. Opin. Cell Biol. 8*:877–889.

* cited by examiner-

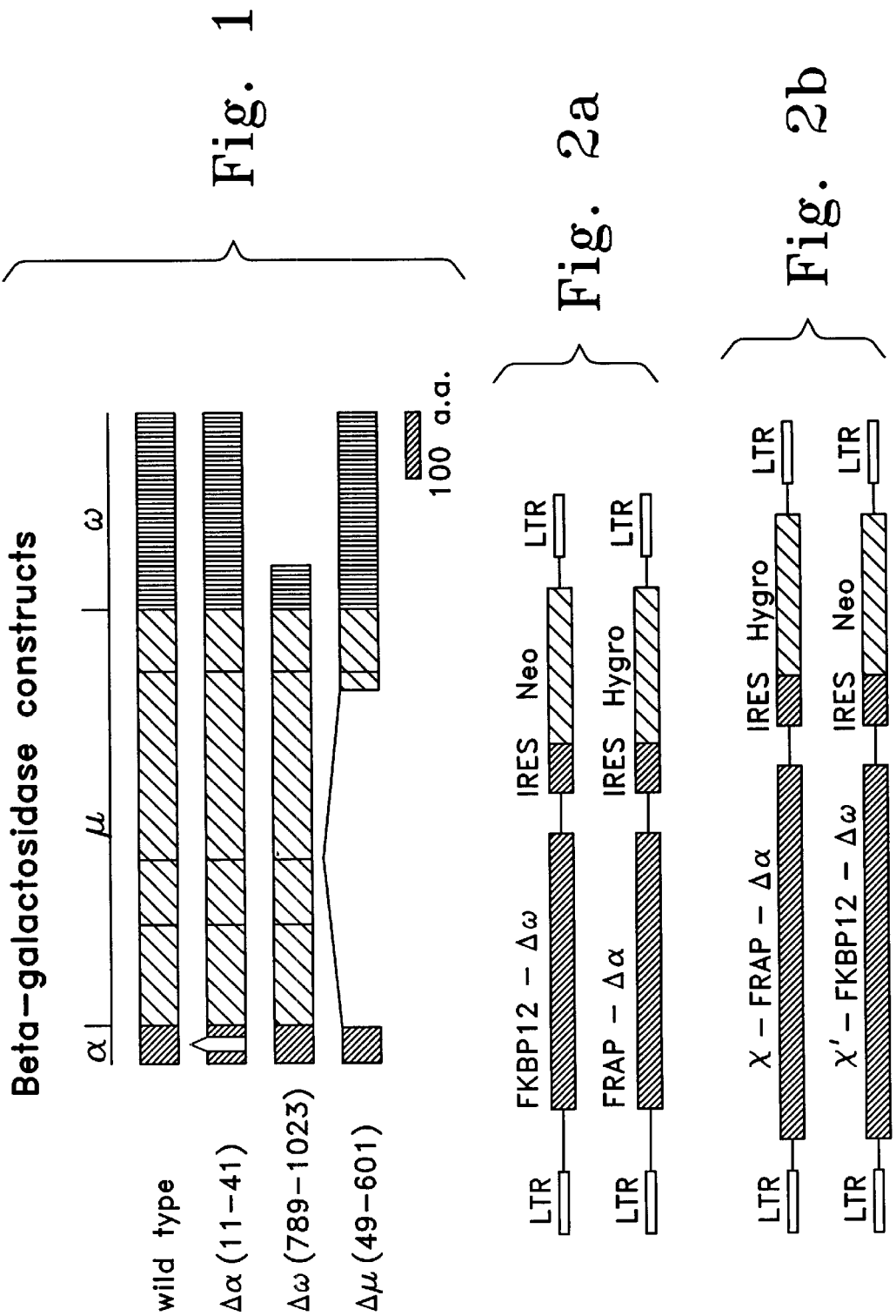

No rapamycin 10 ng/ml rapamycin

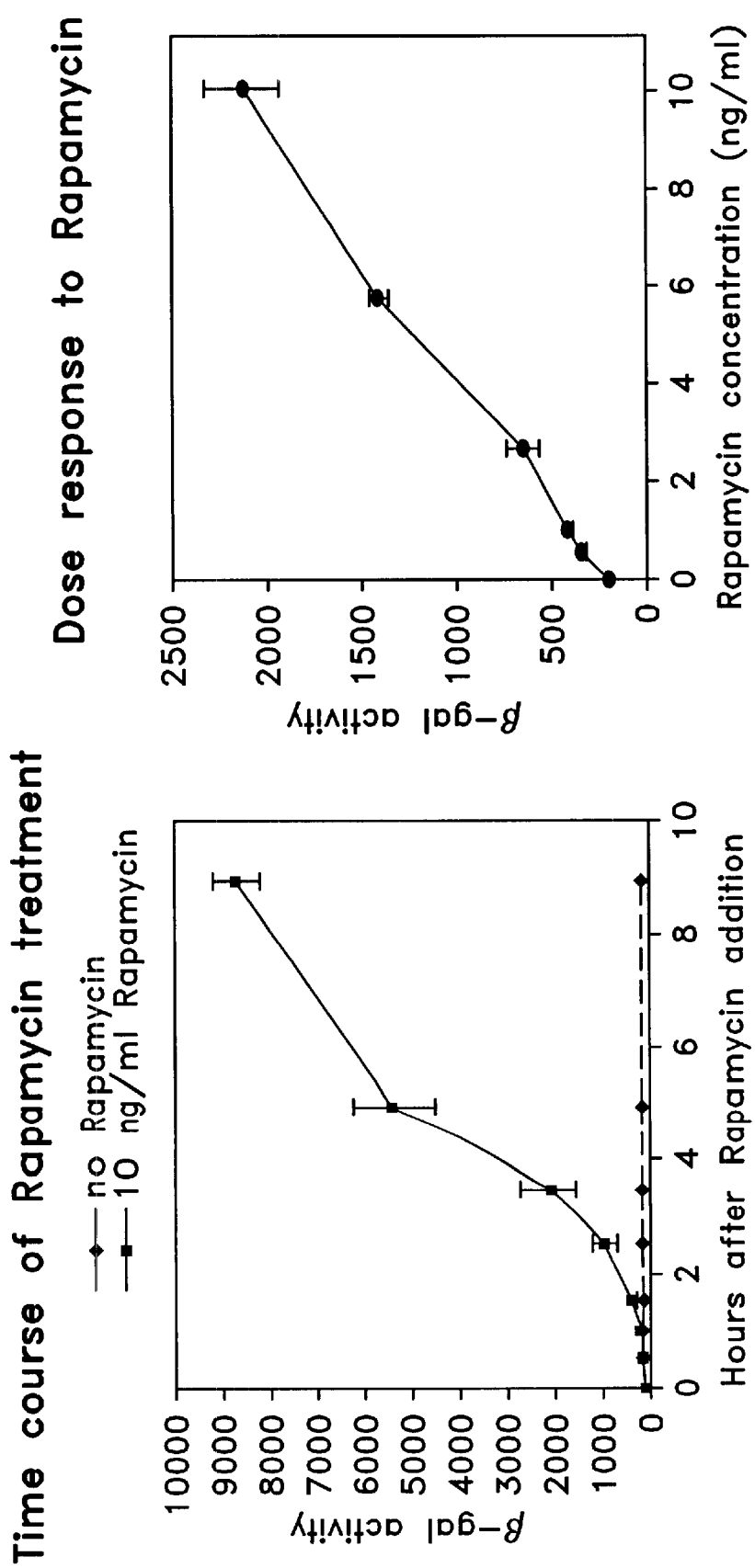

SEQUENCE LISTING

```
<160> NUMBER OF SEQ ID NOS: 2

<210> SEQ ID NO 1
<211> LENGTH: 15
<212> TYPE: DNA
<213> ORGANISM: Artificial Sequence
<220> FEATURE:
<223> OTHER INFORMATION: synthetic construct

<400> SEQUENCE: 1
catggagctc gagag                                                15

<210> SEQ ID NO 2
<211> LENGTH: 24
<212> TYPE: DNA
<213> ORGANISM: Artificial Sequence
<220> FEATURE:
<223> OTHER INFORMATION: synthetic construct

<400> SEQUENCE: 2
gatcaccatg gacgcgtgga tccc                                      24
```

DETECTION OF MOLECULAR INTERACTIONS BY REPORTER SUBUNIT COMPLEMENTATION

CROSS-REFERENCE TO RELATED APPLICATIONS

This application claims priority to the following U.S. Provisional Patent Applications: Ser. No. 60/042,576 filed Apr. 2, 1997 and Ser. No. 60/054,638, filed Aug. 4, 1997; the disclosures of which are hereby incorporated herein by reference in their entireties.

STATEMENT OF RIGHTS TO INVENTIONS MADE UNDER FEDERALLY SPONSORED RESEARCH

This invention was made with Government support under contracts R01 CA 59717 and R01 HD 18179 awarded by the National Institutes of Health. The Government has certain rights in this invention.

TECHNICAL FIELD

This invention is in the field of molecular biology and, more specifically, in the field of reporter systems useful for the analysis of protein-protein interactions.

BACKGROUND

The β-galactosidase enzyme (β-gal), the protein product of the *E. coli* lacZ gene, is widely used in studies of gene expression and cell lineage in higher organisms. Several biochemical assays of β-gal activity, including live-cell flow cytometry and histochemical staining with the chromogenic substrate 5-bromo-4-chloro-3-indolyl β-D-galactopyranoside (X-gal) make the product of the lacZ gene extremely versatile as a quantitative reporter enzyme, selectable marker, or histological indicator. Bronstein et al. (1989) *J. Biolumin. Chemilumin.* 4:99–111; Nolan et al. (1988) *Proc. Natl. Acad. Sci. USA* 85:2603–2607; and Lojda (1979) *Enzyme Histochemistry: A Laboratory Manual*, Springer, Berlin. One property of the lacZ system that has been well-characterized in studies of bacterial genetics, but has not been exploited in eukaryotes is the phenomenon of intracistronic complementation. Studies in *E. coli* have shown that deletions of β-gal which remove portions of either the N-terminus or the C-terminus produce enzyme which is inactive. However, coexpression of one of these deletion mutants with a second inactive deletion mutant containing domains that are lacking in the first can restore β-gal enzymatic activity in a process called complementation. This complemented β-gal activity arises by concentration-dependent assembly of a stable heterooctameric enzyme complex comprising all the essential domains of the wild-type homotetramer. Ullman et al. (1965) *J. Mol. Biol* 12:918–923; Ullman et al. (1967) *J. Mol. Biol* 24:339–343; and Ullman et al. (1968) *J. Mol. Biol.* 32:1–13.

A system utilizing β-gal complementation in enzyme assays has been described. Henderson, U.S. Pat. No. 4,708,929. In this system, enzymatically inactive β-gal polypeptide fragments, capable of combining with high affinity to form active β-gal by complementation, are used. One of the fragments is conjugated to analyte, which allows it to compete with analyte for binding to an analyte-binding protein. If bound to the analyte-binding protein, the β-gal fragment is unable to complement. Thus, by comparing β-gal activity in the presence of sample to that obtained in the presence of a known concentration of analyte (at equal concentrations of analyte-binding protein) the amount of analyte in the sample may be determined. This method requires high-affinity complementing subunits of β-gal, requires that an analyte-binding protein be known, and is not applicable to single-cell analysis.

Previous systems for the study of protein-protein interactions have been described which utilize two fusion genes whose products reconstitute the function of a transcriptional activator. Fields et al., (1989) *Nature* 340:245–247; Bai et al., (1996) *Meth. Enzymol.* 273:331–347; Luo et al., (1997) *BioTechniques* 22(2):350–352. In one fusion gene, a sequence encoding a first protein is conjugated to a sequence encoding a DNA-binding domain of a transcriptional regulatory protein. In a second fusion gene, a sequence encoding a second protein is conjugated to a sequence encoding a transcriptional activation domain of a transcriptional regulatory protein. The two fusion genes are co-transfected into a cell which also contains a reporter gene whose expression is controlled by a DNA regulatory sequence that is bound by the DNA-binding domain encoded by the first fusion gene. Expression of the reporter gene requires that a transcriptional activation domain be brought adjacent to the DNA regulatory sequence. Binding of the first protein to the second protein will bring the transcriptional activation domain encoded by the second fusion gene into proximity with the DNA-binding domain encoded by the first fusion gene, thereby stimulating transcription of the reporter gene. Thus, the level of expression of the reporter gene will reflect the degree of binding between the first and second proteins.

There are several disadvantages associated with the use of the above-mentioned system. As it is dependent upon transcriptionally-regulated expression of a reporter gene, this system is limited to the assay of interactions that take place in the nucleus. In addition, the assay is indirect, relying on transcriptional activation of a reporter gene whose product is diffusible. Hence, a method which would allow a direct and immediate examination of molecular interactions, at the site where they occur, would be desirable.

A system for detecting protein-protein interactions, not limited to nuclear interactions, has been described. U.S. Pat. Nos. 5,503,977 and 5,585,245. In this system, fusions between potential interacting polypeptides and mutant subunits of the protein ubiquitin are formed. Juxtaposition of the two ubiquitin subunits brought about by interaction between potential interacting polypeptides creates a substrate for a ubiquitin-specific protease, and a small peptide reporter fragment is released. In this system, binding between the potential interacting polypeptides does not generate any type of enzymatic activity; therefore, signal amplification is not possible. Additionally, the ubiquitin system does not measure activity in intact cells, but relies on assays of proteolysis in cell-free extracts. What is needed is a sensitive method for examining protein interactions in intact cells in the relevant cellular compartment.

Fluorescence imaging has been used to study the intracellular biochemistry of living cells. A fluorescent indicator for the adenosine 3',5'-cyclic monophosphate (cAMP) signaling pathway has been described in which the sensor is a cAMP kinase in which the catalytic and regulatory subunits each are labeled with a different fluorescent dye, such as fluorescein or rhodamine, capable of fluorescence resonance energy transfer in the holoenzyme complex. A change in shape of the fluorescence emission spectrum occurs upon cAMP binding, and therefore activation of the kinase can be visualized in cells microinjected with the labeled holoenzyme. Adams et al., *Nature,* 349: 694–697 (1991). This system is limited by the fact that it requires microinjection, and a preferred distance between the labeled units for energy transfer to occur.

Substrates for β-lactamase have been described in the art which include a fluorescent donor moiety and a quencher, which include an attached group which makes them permeable through cell membranes, wherein the attached group is hydrolyzed off after the substrate enters the cell. Fluorescence energy transfer between the donor and quencher is monitored as an indicator of β-lactamase activity. This system also can be used in a reporter gene assay using cells containing β-lactamase reporter genes functionally linked to a promoter. PCT WO 96/30540 published Oct. 3, 1996, the disclosure of which is incorporated herein.

DISCLOSURE OF THE INVENTION

The present invention provides methods and compositions for detecting, assaying and quantitating molecular interactions within living cells and in vitro, through complementation between two or more low affinity reporter subunits, such as distinct *E. coli* lacZ mutations. In a preferred embodiment, protein-protein interactions within living cells are detected and quantitated using the methods and compositions of the present invention. The practice of the present invention enables, for the first time, the study of protein-protein interactions and their control in living mammalian cells without reliance upon the transcriptional activation of a reporter gene construct. Association of the proteins of interest results directly in enzyme activity and is independent of other cellular functions. Therefore, the present invention provides advantages over other systems currently in use by allowing the detection of complexes that are excluded from the nucleus, and detection of complexes whose formation would inhibit transcription. Furthermore, the present invention allows the detection and localization of specific binding interactions within cells at different stages of development and differentiation, and an analysis of the induction or inhibition of binding interactions in cells.

Interactions occurring within the nucleus of the cell, interactions occurring in the cytoplasm, on the cell surface, within or on the surface of organelles, or between cytoplasmic and surface (either cellular or organellar) molecules, as well a interactions occurring outside the cell, are all capable of being detected in the practice of the present invention. Thus, the invention surmounts the limitations associated with previous assays for protein-protein interactions, which were either limited to interactions occurring in the nucleus, or did not always allow accurate localization of molecular interactions, and which were not well-suited for detection of interactions which resulted in inhibition of transcription or translation.

Accordingly, in one embodiment, the invention provides a reporter system component comprising:

a first low-affinity reporter subunit, coupled to a first putative binding moiety;

wherein the first low-affinity reporter subunit is capable of association with at least a second low-affinity reporter subunit to generate a detectable signal, said association being mediated by the first putative binding moiety.

In another embodiment, the invention provides a method of determining the occurrence of binding between first and second putative binding moieties, the method comprising:

a) providing a reporter system comprising:

a first component comprising a first low affinity reporter subunit, coupled to the first putative binding moiety; and a second component comprising a second low affinity reporter subunit coupled to the second putative binding moiety;

wherein the first low affinity reporter subunit is capable of association with at least the second low affinity reporter subunit to generate a detectable signal, said association being mediated by the binding of the first and second putative binding moieties;

b) combining the first component and the second component; and c) detecting the presence or absence of the signal.

In a further embodiment, the invention provides a method of screening for binding of a first binding moiety with members of a plurality of different second putative binding moieties, the method comprising:

a) providing a plurality of reporter systems each comprising:

a first component comprising a first low affinity reporter subunit coupled to the first binding moiety, and one of a plurality of second components each comprising a second low affinity reporter subunit coupled to one of said plurality of second putative binding moieties, wherein in each of said second components, said second putative binding moiety is different;

wherein the first low affinity reporter subunit is capable of association with the second low affinity reporter subunit to generate a detectable signal upon the binding of the first binding moiety with one of said different second putative binding moieties;

b) individually combining the first component with each of the plurality of second components to produce a plurality of binding assay samples, each of which includes the first component and a different one of the second components; and c) detecting the presence or absence of the signal in each of the binding assay samples.

The invention additionally provides nucleic acids encoding fusion proteins including a low affinity reporter subunit and a putative binding moiety, and the fusion proteins encoded by said nucleic acids. The invention further provides viral vectors comprising nucleic acids encoding such fusions proteins. The invention also provides cells transformed by the nucleic acids and viral vectors described above.

All patents, patent applications and publications referred to herein are hereby incorporated by reference.

BRIEF DESCRIPTION OF THE DRAWINGS

FIG. 1 is a schematic illustration of three deletion mutant lacZ constructs, designated Δα, Δω and Δμ.

FIG. 2A is a schematic illustration of a viral construct encoding fusion proteins of the Δα or Δω β-gal mutants with either the intracellular FKBP-rapamycin associated protein (FRAP) or the intracellular rapamycin binding protein, FK506-binding protein-12 (FKBP12) upstream of the hygromycin or neomycin resistance genes.

FIG. 2B is a schematic illustration of a viral construct encoding fusion proteins of the Δα or Δω β-gal mutants with either FRAP or FKBP12 and another protein, represented as x and x', upstream of the hygromycin or neomycin resistance genes.

FIG. 4A is a graph of β-gal activity vs. time with and without rapamycin treatment of C2C12 cells expressing both FKBP12-Δω and FRAP-Δα fusion proteins.

FIG. 4B is a graph of the dose-response to rapamycin of the activity of β-gal in C2C12 cells expressing both FKBP12-Δα and FRAP-Δα fusion proteins.

In FIGS. 6A, 6B and 6C, the vertical axis represents cell number and the horizontal axis represents intensity of β-gal fluorescence expressed on a logarithmic scale.

FIG. 7A depicts schematically the rationale of the assay: two weakly complementing deletion mutants of β-gal are linked to the extracellular and transmembrane domains of the EGF receptor. Receptor dimerization, stabilized by EGF, will drive β-gal complementation.

FIG. 7B shows the design of the retroviral constructs used in the assay. *E. coli* lacZ deletion mutants Δα and Δω were cloned into pWZL vectors expressing neomycin or hygromycin resistance, respectively. The extracellular and transmembrane (tm) domains of human EGF receptor were cloned in frame with the Δα and Δω mutants.

FIG. 7C shows FACS analysis of a population of transduced and selected cells. EGF treatment increases the β-gal activity (fluorescein fluorescence) in a substantial proportion of the cells. The FACS profile of cells without EGF treatment is shaded in light gray and is outlined in white. The profile of cells treated with EGF is shaded dark gray.

FIG. 7D shows FACS analysis of chimeric receptor expression, using a monoclonal antibody to the extracellular domain of the human EGF receptor. The FACS profile of the transduced and selected population is shaded medium gray and outlined in white; untransduced cells are shaded light gray and outlined in white. The FACS was used to clone cells that had low β-gal activity in the absence of EGF and showed increased β-gal activity in the presence of EGF. One clone that had low levels of the chimeric receptor relative to the population (shaded in dark gray) was used for further analyses.

FIG. 7E shows induction of EGF receptor dimerization (β-gal activity) in all of the cells of the clone selected in FIG. 7D, upon treatment with 100 ng/ml EGF for two hours. Untreated cells are shaded in light gray and outlined in white; EGF treated cells are shaded in dark gray.

FIG. 7F shows that dimerization can be detected after very short treatments with EGF. Cells were treated with 100 ng/ml EGF for 0, 1, 4, 8, and 15 minutes before cells were rinsed and processed for FACS analysis. The mean fluorescence of the cell sample is plotted.

FIG. 9A shows, in the left panel, schematic diagrams of different regimens for treatment of cells with EGF, tyrphostin, or both. After the various treatments, cells were analyzed on the FACS, and the mean fluorescence is shown in the right panel. Each treatment was performed in triplicate.

FIG. 9B shows measurements of β-galactosidase activity in EGF-treated cells compared with EGF+tyrphostin-treated cells. Cells expressing the chimeric receptor were treated with either 100 ng/ml EGF (-■-) or EGF and 100 nM tyrphostin AG1478 for 0 to 24 hours (--▲--). Triplicate samples were analyzed for each time point, and the error bars indicate the standard deviation of the replicate samples.

MODES FOR CARRYING OUT THE INVENTION

Definitions

Figure 3A:
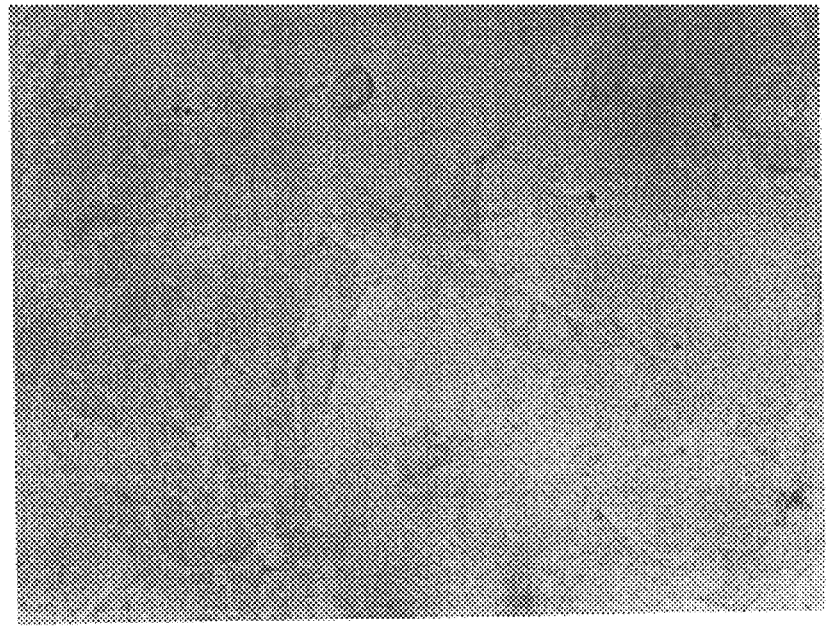
FIGS. 3A and 3B show X-gal staining of fixed cells expressing both FKBP12-Δω and FRAP-Δα. Cells shown in 3*b* were exposed to 10 ng/ml rapamycin for 12 hr. Cells shown in 3*a* were not exposed to rapamycin.

As used herein, the following terms have the following definitions:

As used herein, a "reporter subunit" refers to a member of a complex of two or more subunits which are capable of associating with low binding affinity with each other to generate a detectable signal, or which are capable of associating with each other and one or more additional substances to generate a detectable signal, and which do not individually generate the detectable signal.

As used herein, "low affinity" reporter subunits refer to molecular species which have a sufficiently low binding affinity for each other such that when they each are covalently attached to two different binding moieties, they substantially do not become associated unless a binding interaction between the two binding moieties occurs. "Low affinity" thus generally refers to a binding affinity which is at least less than that of the attached binding moieties.

As used herein, "binding moieties" refers to at least two molecular species, such as proteins or fragments thereof, which interact with each other to form a stable complex.

As used herein, a "detectable signal" refers to any detectable signal which occurs upon the association of the reporter subunits or via the interaction of the associated subunits with another substance. The detectable signal may be for example, a chromogenic, fluorescent, phosphorescent or chemiluminescent signal, such as a detectable product of an enzymatic reaction catalyzed by the associated reporter subunits.

The terms "protein", "polypeptide", and "peptide" are used interchangeably herein to refer to polymers of amino acids of any length. The polymer may be linear or branched, it may comprise modified amino acids, and it may be interrupted by non-amino acids. It also may be modified naturally or by intervention; for example, disulfide bond formation, glycosylation, myristylation, acetylation, alkylation, phosphorylation or dephosphorylation. Also included within the definition are polypeptides containing one or more analogs of an amino acid (including, for example, unnatural amino acids) as well as other modifications known in the art.

Unless otherwise indicated, the practice of the present invention will employ conventional techniques of molecular biology, biochemistry, microbiology, recombinant DNA, nucleic acid hybridization, genetics, immunology, embryology and oncology which are within the skill of the art. Such techniques are explained fully in the literature. See, for example, Maniatis, Fritsch & Sambrook, MOLECULAR CLONING: A LABORATORY MANUAL, Cold Spring Harbor Laboratory Press (1982); Sambrook, Fritsch & Maniatis, MOLECULAR CLONING: A LABORATORY MANUAL, Second Edition, Cold Spring Harbor Laboratory Press (1989); Ausubel, et al., CURRENT PROTOCOLS IN MOLECULAR BIOLOGY, John Wiley & Sons (1987, 1988, 1989, 1990, 1991, 1992, 1993, 1994, 1995, 1996).

Reporter Subunits

As used herein, a "reporter subunit" refers to a member of a complex of two or more subunits which are capable of associating with low binding affinity with each other to generate a detectable signal, or which are capable of associating with each other and one or more additional substances to generate a detectable signal, and which do not individually generate the detectable signal.

The detectable signal thus provides an indication that the subunits have become associated. In general, in an assay of the binding affinity of a first and at least a second molecular species (the "putative binding moiety"), a first component is provided which includes one reporter subunit attached to the first molecular species, and a second component is provided which includes another of the same or different reporter subunit attached to the second molecular species. The reporter subunits preferably have sufficiently low binding affinity for each other such that they substantially do not associate with each other in solution unless and until the molecules for which binding affinity is being assayed have sufficient binding affinity to mediate complex formation between the two components. Upon binding of the binding moieties and resulting association of the reporter subunits, generally by non-covalent interactions, such as hydrogen bonding or hydrophobic interactions, for example, the reporter subunits are oriented close enough to each other such that they are capable of associating with low affinity and generating a detectable signal. In the system, individual reporter subunits are not able to generate the detectable signal. Thus, the reporter subunits undergo forced complementation when brought into close proximity.

The reporter subunits can be designed to have a preferred low affinity for a particular application and for the conditions in which the binding assay is done. Binding of molecules will depend upon factors in solution such as pH, ionic strength, concentration of components of the assay, and temperature. In the binding assays using reporter systems described herein, the binding affinity of the reporter subunits should be low enough to permit forced complementation. Non-limiting examples of dissociation constants of the reporter subunits in an assay solution, such as a buffered system or cell interior, are on the order of greater than about $10^{-8}$M for example, greater than $10^{-6}$ M or optionally, between about $10^{-2}$ to $10^{-5}$M depending upon the properties of the particular assay system.

Reporter subunits which have sufficiently low binding affinity, and yet are still capable of associating and generating a detectable signal upon the binding of molecular species attached to them can be designed as disclosed herein. Reporter subunits which can be used include any low binding affinity subunits which are capable of associating to produce a detectable signal. In one preferred embodiment, the reporter subunits are proteins which are capable of associating and are capable when associated of catalyzing a reaction which produces a directly or indirectly detectable product.

Protein enzymes capable of catalyzing conversion of a substrate to a detectable reaction product, either directly or indirectly, which have been used, for example, in cell based screening assays may be used as reporter subunits. The enzymes can be modified into reporter subunits and to have a low binding affinity and the ability to undergo forced complementation. These may be modified, for example, by site directed or random mutagenesis, or deletion mutation, to provide low affinity subunits which are capable of associating with low binding affinity and thereby undergo complementation to catalyze an enzymatic reaction. For example, reporter subunits capable of complementation with low binding affinity may be derived from enzymes such as β-galactosidase, β-glucuronidase (GUS), β-lactamase, alkaline phosphatase, peroxidase, chloramphenicol acetyltransferase (CAT) and luciferase. Any of a range of enzymes capable of producing a detectable product either directly or indirectly may be so modified or may occur naturally. Additionally, reporter subunits may be derived from non-enzymatic molecules. For example, association of two proteins may generate a unique conformation in one or both of the interacting proteins that can be recognized by an antibody or other ligand.

β-galactosidase, which is encoded by the *E. coli* lacZ gene, is an enzyme which has been developed in the art as reporter enzyme. β-galactosidase activity may be measured by a range of methods including live-cell flow cytometry and histochemical staining with the chromogenic substrate 5-bromo-4-chloro-3-indolyl β-D-galactopyranoside (X-Gal). Nolan et al., *Proc. Natl. Acad. Sci., USA*, 85:2603–2607 (1988); and Lojda, Z., *Enzyme Histochemistry: A Laboratory Manual*, Springer, Berlin, (1979), the disclosures of which are incorporated herein.

Enzyme mutants capable of intracistronic complementation are especially suitable as reporter subunits. In *E. coli*, deletions of either the N or C terminus of β-gal produce enzyme that is inactive yet can be complemented by coexpression with a second inactive deletion mutant containing domains lacking in the first. The N- and C- terminal domains involved in complementation are known as the α and ω regions. Ullmann et al., *J. Mol. Biol.*, 12:918–923 (1965); Ullman et al., *J. Mol. Biol.*, 24:339–343 (1967); and Ullman et al., *J. Mol Biol.*, 32:1–13 (1968), the disclosures of which are incorporated herein. β-Gal complementation systems in mammalian cells are described in Mohler and Blau, *Proc. Natl. Acad. Sci. USA,* 93:12423–12427 (1996), the disclosure of which is incorporated herein. As described therein, vectors expressing complementing mutants of β-gal may be constructed. A naturally occurring lacZ mutation, ΔM15 (Beckwith, *J. Mol. Biol.*, 8:427–430 (1964); and Prentki, *Gene*, 122:231–232 (1992) and *Nature,* 369:761–766 (1994), the disclosures of which are incorporated herein) designated as Δα herein may be constructed. Another deletion mutation, designated Δω herein, was made as disclosed herein, and its structure is shown schematically in FIG. 1. The peptide region between the α and ω regions is referred to herein as the μ region, as first defined by Mohler and Blau, *Proc. Natl. Acad. Sci. USA*, 93:12423–12427 (1996). The Δα and Δω mutants are demonstrated herein to have optimal forced complementation properties. These deletion mutants express polypeptides representing an α-acceptor/ω-donor (Δα) and an α-donor/ω-acceptor (Δω).

β-Gal complementation is based on the ability of mutant enzyme molecules to associate and reconstitute an active enzyme. Accordingly, two β-gal molecules that each lack one or more structural domains critical to the activity of the holoenzyme, associate to form a single functional unit that contains all of the required structural determinants. This phenomenon is dependent on the fact that interactions that would normally take place between domains of the single peptide of wild type β-gal, can also exist between domains present on two distinct peptides, leading to the formation of a stable dimer. This dimer behaves functionally as a single peptide of wild type β-gal, and participates ultimately in the formation of the tetramer that represents the active form of the enzyme. Thus, the ability of a pair of β-gal mutants to recreate an active form of the enzyme is strongly dependent on their ability to form a stable dimer and therefore would be expected to be dependent on their affinity for each other.

Surprisingly, it has been discovered that forced association or complementation of two distinct low affinity β-gal mutants results in an efficient formation of active enzyme molecules in mammalian cells even though they have relatively low affinity for each other. The forced complementation results when the two mutant subunits are brought into association due to the binding affinity of the binding moieties attached to the mutant subunits. By engineering constructs in which domains or proteins of interest drive the dimerization between Δα and Δω β-gal mutants, it is possible to monitor and quantitate such interactions by assessing the efficiency of complementation obtained by coexpression of these fusion proteins in intact eucaryotic cells.

In addition to two-component complementation between Δα and Δω β-gal mutants, the invention also contemplates three-component complementation among mutants each of which contains only a single functional α, μ, or ω region. Among other applications, this might allow detection of interactions among three distinct proteins based on a single reporter. Similarly, higher-order systems containing four or more reporter components are within the scope of the invention.

Using the fused protein systems, protein-protein interactions and their regulation can be studied in mammalian cells without relying on the transcriptional activation of a reporter construct. Association of the proteins of interest directly results in enzyme activity and is independent from other cellular functions. Therefore this system allows the detection of complexes that are excluded from the nucleus, or that involve partners that inhibit transcription. Furthermore it allows the detection, quantitation and determination of the localization of specific binding interactions within cells, as well as the temporal distribution of such binding interactions. Binding interactions may be compared in cells at different stages of development or differentiation, as well as in normal vs. pathologic cells and in infected vs. uninfected cells, to give but a few examples. Binding interactions can therefore be assessed against a background of endogenous competing components that may differ in nature and in concentration among different cell types.

Other enzymes may be identified or constructed which are capable of forced complementation in the reporter systems described herein. For example, the phenomenon of intracistronic complementation of enzymatic activity has been described for tryptophan synthetase. Jackson et al. *J. Biol. Chem.*, 244:4539–4546 (1969). Complementation between mutant subunits of thymidylate synthase has been described. Pookanjanatavip et al., *Biochemistry* 31:10303–10309 (1992), the disclosure of which is incorporated herein. Thus, reporter subunits derived from any complementing enzyme system known in the art can be used in the practice of the present invention. Mutants can be derived from other enzymes or proteins that are capable of serving as reporters of protein-protein interactions, or whose activity can be regulated as described above. The system exploits the complementation ability of low binding affinity enzyme mutants for detection of protein-protein interactions.

For example, complementing low affinity reporter subunits derived from β-lactamase can be constructed. Activity of the complementing β-lactamase can be detected using substrates for β-lactamase developed in the art which include a fluorescent donor moiety and a quencher, which include an attached group which makes them permeable through cell membranes, wherein the attached group is hydrolyzed off after the substrate enters the cell. Fluorescence energy transfer between the donor and quencher then can be monitored as an indicator of β-lactamase activity, as described in PCT WO 96/30540 published Oct. 3, 1996.

In addition to enzymes which catalyze a reaction to produce a detectable product, proteins, protein domains or protein fragments which are themselves detectable upon association can be used. Exemplary proteins include green fluorescent proteins, which have characteristic detectable emission spectra, and have been modified to alter their emission spectra, as described in PCT WO 96/23810, the disclosure of which is incorporated herein. Fusions of green fluorescent proteins with other proteins, and DNA sequences encoding the fusion proteins which are expressed in cells are described in PCT WO 95/07463, the disclosure of which is incorporated herein.

Other exemplary subunits include subunits which are capable of associating to produce a photochemical signal such as a fluorescent or luminescent signal, including chemiluminescent or photoluminescent signals. The reporter subunits also may comprise fluorophores which are capable of detectable resonance energy transfer when they are closely associated, as disclosed, for example, in EP Publication No. 0 601 889 A2 and PCT WO 96/41166, the disclosures of which are incorporated herein.

Other complementing enzymes are known in the art, for example, pancreatic ribonuclease and Staphylococcal nuclease. Mutants of the complementing subunits of these enzymes can be constructed, by methods well-known to those of skill in the art such as site-directed mutagenesis, to generate low-affinity complementing subunits. One possible use for these types of complementing protein is as a tumor therapeutic, wherein a tumor-specific protein serves as a bridge to bring together two proteins, each of which is fused to a low-affinity complementing fragment of the nuclease. The resultant nuclease activity might, in some cases, kill the cell by destroying mRNA, genomic DNA, etc.

Binding Moieties

Binding moieties which can be assayed for their binding affinity with each other include any molecules capable of a binding interaction. The binding interaction between the two or more binding moieties may be either direct or in the form of a complex with one or more additional binding species, such as charged ions or molecules, ligands or macromolecules.

The binding moieties which are attached to the reporter subunit can be any of a range of different molecules including carbohydrates, lipids, proteins, and nucleic acids, as well as portions, polymers and analogues thereof, provided they are capable of being linked to the reporter subunit. Exemplary proteins include members of a signal transduction cascade, proteins regulating apoptosis, proteins that regulate progression of the cell-cycle or development of tumors, transcriptional regulatory proteins, translational regulatory proteins, proteins that affect cell interactions, cell adhesion molecules (CAMs), ligand-receptor pairs, proteins that participate in the folding of other proteins, and proteins involved in targeting to particular intracellular compartments, such as the Golgi apparatus, endoplasmic reticulum, ribosomes, chloroplasts and mitochondria.

Other exemplary proteins include protein hormones and cytokines. Cytokines include those involved in signal transduction, such as interferons, chemokines, and hematopoietic growth factors. Other exemplary proteins include interleukins, lymphotoxin, transforming growth factors-α and β, and macrophage and granulocyte colony stimulating factors. Other proteins include intracellular enzymes such as protein kinases, phosphatases and synthases.

Exemplary proteins involved in apoptosis include tumor necrosis factor (TNF), Fas ligand, interleukin-1β converting enzyme (ICE) proteases, and TNF-related apoptosis-inducing ligand (TRAIL). Proteins involved in the cell cycle include deoxyribonucleic acid (DNA) polymerases, proliferating cell nuclear antigen, telomerase, cyclins, cyclin dependent kinases, tumor suppressors and phosphatases. Proteins involved in transcription and translation include ribonucleic acid (RNA) polymerases, transcription factors, enhancer-binding proteins and ribosomal proteins. Proteins involved in cellular interactions such as cell-to-cell signaling include receptor proteins, and peptide hormones or their enhancing or inhibitory mimics.

Binding of molecules will depend upon factors in solution such as pH, ionic strength, concentration of components of the assay, and temperature. In the binding assays using reporter systems described herein, the binding affinity of the binding moieties should be high enough to permit forced complementation between the reporter subunits. Non-limiting examples of dissociation constants of the binding moieties in an assay solution, such as a buffered system or cell interior, are on the order of less than about $10^{-8}$ M, for example, less than about $10^{-9}$ M, or optionally, between about $10^{-9}$ to $10^{-12}$M, depending upon the properties of the particular assay system.

Linking of the Reporter Subunit and the Binding Moiety

The reporter subunit and one or more binding moieties are generally linked either directly or via a linker, and are generally linked by a covalent linkage. For example, when the reporter subunit and the binding moiety are proteins, they may be linked by methods known in the art for linking peptides.

In one preferred embodiment, the reporter subunit and the binding moiety comprise a fusion protein including the reporter subunit which is a low binding affinity enzyme complement and the binding moiety being assayed. The fusion protein can thus be expressed from an encoding nucleic acid intracellularly. This system is advantageous since it permits the detection and quantitation of protein-protein interactions in cells, such as mammalian cells, based on enzymatic complementation of the low affinity reporter subunits.

For example, in the embodiment wherein chimeric fused proteins are produced intracellularly that include one of two complementing low affinity β-gal mutants and a "test" protein of interest, the detected β-gal activity due to interactions between two chimeric proteins of interest will be proportional to the strength of the interaction of the non-β-gal protein components. Thus, the interaction is driven by the test proteins of interest, not the complementing mutants. The enzymatic activity serves as an indicator of that interaction. Another advantage of this system is that only low levels of expression of the test proteins are required to detect binding.

The fusion gene constructs preferably are constructed and transformed into cells to produce low level expression. The system then permits the monitoring of interactions in a given cell in the presence of endogenous competing protein partners, where the fusion protein will function as a "tracer" for the binding/association reaction. Such a system will not be prone to artifacts arising from overexpression of introduced proteins. Reduction in expression of fusion gene constructs can be accomplished by choice of appropriate promoters, ribosome binding sites and other regulatory elements. For example, fusion gene constructs can be introduced into vectors in which they lie upstream of an antibiotic resistance gene whose translation is regulated by the Encephalomyocarditis virus internal ribosome entry sequence (IRES), and which contain a mutation in the splice donor/acceptor sequences upstream of the ATG sequence responsible for translational initiation of the fusion gene. This type of construct results in a lower translation efficiency of the first coding sequence in a bicistronic message, but does not affect translation of the second (antibiotic resistance) sequence, which is solely dependent on the IRES. As a result of these reduced levels of expression, the frequency of spontaneous interaction of reporter subunits, which is concentration-dependent, will be significantly reduced.

Expression of Fusion Proteins

The invention provides fusion proteins between a putative binding moiety and a low affinity reporter subunit. The putative binding moiety may comprise any protein or other molecule whose ability to bind to a second molecule is to be tested. The low affinity reporter subunit may be any molecule wherein the monomer subunit is inactive, but association of two or more identical or different monomers restores activity. The activity must be capable of generating a detectable signal. In a preferred embodiment, the low affinity reporter subunits comprise mutants of β-galactosidase capable of complementation with one another.

Fusion proteins comprise a single continuous linear polymer of amino acids which comprise the full or partial sequence of two or more distinct proteins. The construction of fusion proteins is well-known in the art. Two or more amino acids sequences may be joined chemically, for instance, through the intermediacy of a crosslinking agent. In a preferred embodiment, a fusion protein is generated by expression of a fusion gene construct in a cell. A fusion gene construct comprises a single continuous linear polymer of nucleotides which encodes the full or partial sequences of two or more distinct proteins in the same uninterrupted reading frame. Fusion gene constructs generally also contain replication origins active in eucaryotic and/or procaryotic cells and one or more selectable markers encoding, for example, drug resistance. They may also contain viral packaging signals as well as transcriptional and/or translational regulatory sequences and RNA processing signals.

The fusion gene constructs of the invention are introduced into cells to assay for binding between the putative binding moieties encoded by the fusion gene constructs. The fusion gene constructs may also contain promoters and other transcriptional and/or translational regulatory sequences that are normally associated with the gene encoding the putative binding moiety. The fusion gene constructs may be introduced into cells by any method of nucleic acid transfer known in the art, including, but not limited to, viral vectors, transformation, co-precipitation, electroporation, neutral or cationic liposome-mediated transfer, microinjection or gene gun. Viral vectors include retroviruses, poxviruses, herpesviruses, adenoviruses, and adeno-associated viruses. Particularly preferred in the present invention are retroviral vectors, which are capable of stable integration into the genome of the host cell. For example, retroviral constructs encoding integration and packaging signals, drug resistance markers and one or more fusion genes of interest are useful in the practice of the invention.

Different fusion gene constructs encoding unique fusion proteins may be present on separate nucleic acid molecules or on the same nucleic acid molecule. Inclusion of different fusion gene constructs on the same nucleic acid molecule is advantageous, in that uptake of only a single species of nucleic acid by a cell is sufficient to introduce sequences encoding both putative binding partners into the cell. By contrast, when different fusion constructs are present on different nucleic acid molecules, both nucleic acid molecules must be taken up by a particular cell for the assay to be functional. Thus, problems of cell mosaicism are avoided when both fusion gene constructs are included on the same nucleic acid molecule.

The fusion gene constructs or fusion proteins of the invention may be introduced into cultured cells, animal cells in vivo, animal cells ex vivo, or any other type of cell in which it is desired to study protein-protein interactions.

Assays

The reporter systems disclosed herein may be used to assay binding interactions of putative binding moieties attached to low affinity reporter subunits through complementation between the low affinity reporter subunits which produces a detectable signal. In addition to testing for direct binding interactions between the putative binding moieties, interactions dependent upon one or more additional molecules or ions may be evaluated. Further, multi-molecular interactions in living animal cells can be evaluated, as well as the influence of various drugs, peptides and pharmaceuticals on these interactions.

In one embodiment, the binding affinity of one or more putative binding moieties may be measured by providing a reporter system including one component having one of the moieties bound to a low affinity reporter subunit and at least one other component including one other putative binding moiety bound to a second low affinity reporter subunit. The binding moieties may be different or the same. In the system, the reporter subunits are capable of binding and generating a detectable signal only if they are brought into proximity by the binding of the one or more putative binding moieties. The signal can be directly or indirectly detected and quantitated.

In one embodiment of the invention, protein-protein interactions can be detected and quantitated. The signal produced by the complementing reporter subunits can serve as an indicator of binding between the putative binding moieties, either directly or indirectly via a third substance. Signals which could be detected include light emission and absorbance. Exemplary signals include chromogenic, fluorescent and luminescent signals. These signals can be detected and quantitated visually or through the use of spectrophotometers, fluorimeters, microscopes, scintillation counters or other instrumentation known in the art.

Binding of components of the reporter systems disclosed herein will depend upon factors in solution, such as pH, ionic strength, concentration of components of the assay, and temperature. Assay solutions can be designed and developed for a particular system. The reporter systems disclosed herein can be used to conduct assays in solutions, such as buffered cell free solutions, cell interiors, solutions of cells, solutions of cell lysates, and solutions of cell fractions, such as nuclear fractions, cytoplasmic fractions, mitochondrial fractions, and membrane fractions. Methods for preparing assay solutions, such as enzyme assay solutions, cell extracts, and cell suspensions, known in the art may be used. For example, physiologically compatible buffers such as phosphate buffered saline may be used. See for example, the series, Methods in Enzymology, Academic Press, New York.

In one embodiment, the low affinity reporter subunits are capable of complementing one another to form an enzymatically active complex that is capable of catalyzing the conversion of a substrate to a product which is detectable, either directly or indirectly. In one embodiment, the reporter system can include two or more components, each of which is a fusion protein, wherein the fusion proteins each comprise a putative binding protein fused to a low affinity reporter subunit. Thus, nucleic acids encoding the fusion proteins can be constructed, introduced into cells and expressed in cells. Alternatively, the bound reporter units or bound binding moieties can be detecting by detecting the binding of a labeled specific binding moiety such as an antibody to the bound complex.

In one embodiment, the low affinity reporter subunits may be complementing subunits of β-gal. The system may include three or more reporter subunits all of which are required to associate in order to produce the detectable signal. Methods for detecting the reaction products of active β-gal that have been developed in the art may be used. For example, β-galactosidase activity may be measured by a range of methods including live-cell flow cytometry and histochemical staining with the chromogenic substrate 5-bromo-4-chloro-3-indolyl β-D-galactopyranoside (X-Gal). Nolan et al., *Proc. Natl. Acad. Sci, USA*, 85:2603–2607 (1988); and Lojda, Z., *Enzyme Histochemistry: A Laboratory Manual*, Springer, Berlin, (1979), the disclosures of which are incorporated herein. Histochemical staining for β-gal can be achieved by fixation of cells followed by exposure to X-gal.

Assays for β-gal activity described in Mohler and Blau, *Proc. Natl. Acad. Sci.*, 93:12423–12427 (1996), the disclosure of which is hereby incorporated by reference, may be used. In one embodiment, intracellular analyses may be conducted by fixing cells and staining with the indigogenic substrate X-gal. Fixed cells also can be analyzed by assaying for β-gal activity by fluorescence histochemistry using an azo dye in combination with either X-gal or 5-bromo-6-chloro-3-indolyl β-D-galactopyranoside (5-6-X-Gal). A preferred combination is the azo dye red violet LB (Sigma Chemical, St. Louis, Mo.) and 5-6-X-Gal, referred to as Fluor-X-gal. For this combination, fluorescence micrographs can be obtained on a fluorescence microscope using a rhodamine/Texas Red filter set. Use of these substrates allows, for the first time, β-gal-dependent fluorescence to be visualized simultaneously with two or more other fluorescent signals.

Vital substrates for β-gal, which can be used in living cells, are also encompassed by the invention. For example, a vital fluorogenic substrate, resorufin β-galactoside bis-aminopropyl polyethylene glycol 1900 (RGPEG) has been described. Minden (1996) *BioTechniques* 20(1):122–129.

This compound can be delivered to cells by microinjection, electroporation or a variety of bulk-loading techniques. Once inside a cell, the substrate is unable to escape through the plasma membrane or by gap junctions. Another vital substrate that can be used in the practice of the invention is fluorescein di-β-D-galactopyranoside (FDG), which is especially well-suited for analysis by fluorescence-activated cell sorting (FACS) and flow cytometry. Nolan et al. (1988) *Proc. Natl. Acad. Sci. USA* 85:2603–2607 and Rotman et al. (1963) *Proc. Natl. Acad. Sci. USA* 50:1–6.

β-gal may also be detected using a chemiluminescence assay. For example, cells containing β-gal fusions are lysed in a mixture of buffers containing Galacton Plus substrate from a Galactolight Plus assay kit (Tropix, Bedford Mass.). Bronstein et al, *J. Biolumin. Chemilumin.*, 4:99–111 (1989) the disclosure of which is incorporated herein. After addition of Light Emission Accelerator solution, luminescence is measured in a luminometer or a scintillation counter.

Reporter systems other than β-gal may also be used in the practice of the invention. For example, the enzyme β-glucuronidase (GUS) can be used as a reporter and chromogenic and fluorogenic GUS substrates have been developed. The GUS substrate 5-bromo-4-chloro-3-indolyl β-D-glucuronic acid (X-gluc) can be used in both chromogenic and fluorogenic applications, as follows. In one method of chromogenic staining, fixed cells are washed in PBS and stained with 2 mM X-gluc (Molecular Probes, Eugene OR), 10 mM EDTA, 0.5 mM $K_3Fe(CN)_6$, 0.5 mM $K_4Fe(CN)_6$, 0.1% Triton X-100, 0.1 M $NaPO_4$. Fluorogenic staining may be achieved by using a combination of 5-bromo-6-chloro-3-indolyl β-D-glucuronic acid (5, 6 X-gluc, Molecular Probes, Eugene, Oreg.) and Fast Red Violet LB (Sigma Chemical, St. Louis, Mo.). Fixed cells are rinsed with PBS and stained in 50 μg/ml 5, 6 X-gluc and 100 μg/ml Fast Red Violet LB, then rinsed in PBS. Fluorescence is detected on a fluorescence microscope adjusted for detection of rhodamine fluorescence.

In one embodiment of the invention, the reporter subunits comprise an enzyme and an inhibitor of the enzyme. Preferably, the inhibitor has a low affinity for the enzyme. In this case, association between the putative binding moieties is evidenced by inhibition of the activity of the enzyme. Exemplary enzymes include β-gal, GUS, β-lactamase, etc.

While dimeric reporter subunit complexes are discussed herein by way of example, multimeric reporter subunits also can be used, as can reporter subunits which are only active in the presence of one or more additional molecules or atoms. An example of a trimeric reporter subunit system would be one consisting of a β-gal ω donor (such as a $\Delta\alpha$-$\Delta\mu$ double mutant), a β-gal μ donor (such as a $\Delta\alpha$-$\Delta\omega$ double mutant) and a β-gal α donor (such as a $\Delta\mu\Delta\omega$ double mutant), wherein each individual mutant, and any pairwise combination of two mutants, is enzymatically inactive. Activity would be obtained only if all three subunits were able to associate with one another. Enzyme reaction products can be detected using methods available in the art, such as biochemical assay, microscopy, flow cytometry, light emission or absorption detection, and immunological methods.

The methods disclosed herein enable the detection and quantitation of binding events in cell lysates, as well as in intact cells. Thus, interactions between fully folded proteins are detectable, and co-translational expression of the binding moieties is not necessary for binding to be detected.

In the practice of the invention, the reaction product may be detected indirectly, for example, through immunological techniques, such as immunofluorescent labeling.

Protein-protein interactions can be measured in a reporter system which includes one or more fusion proteins. The fusion proteins each include a putative binding protein coupled to a low affinity reporter subunit. For intracellular expression of the fusion proteins, one or more fusion gene constructs are prepared which include sequences encoding the fusion protein(s). The fusion gene constructs may be introduced into cells by methods available in the art, including, but not limited to, viral vectors, transformation, co-precipitation, electroporation, neutral or cationic liposome-mediated transfer, microinjection or gene gun.

A variety of cell-based assays can be conducted using the cells containing the fusion gene constructs. Binding of the putative binding moieties on the fusion proteins expressed in the cells can be confirmed by detecting the signal produced by the reporter subunits undergoing forced complementation. Thus, for example, when the reporter subunits are complementing β-gal subunits, cells exhibiting β-gal activity indicate binding between the putative binding moieties within those cells.

The fusion gene constructs may also contain promoters and other transcriptional and/or translational regulatory sequences that are normally associated with the gene encoding the putative binding moiety. This permits the study of physiologically-relevant levels of the putative binding proteins in vivo, in contrast to systems in which test proteins are overexpressed. Further, this permits the study of naturally-occurring changes in levels of binding activity over time and can reveal the effects of endogenous or exogenous substances on binding interactions.

The methods and compositions of the invention can also be used to study other molecules which influence the interaction of two putative binding partners. Proteins, peptides, nucleic acids, carbohydrates, lipids, ions, small molecules, synthetic compounds or other substances (either endogenous to the cell or exogenously added) may act as either agonists or antagonists of a binding interaction. By measuring the effect of such molecules on, for example, β-gal activity produced by cells containing two or more fusions representing a particular pair of test proteins, agonist or antagonist activity of such molecules can be determined. Use of the methods and compositions of the invention will allow high-throughput assays to be carried out to test for agonists or antagonists of a particular binding interaction. Such high-throughput assays will be especially valuable in screening for drugs that influence medically-relevant protein-protein interactions.

Putative binding partners, or putative binding moieties, as used in the invention, can include molecules which do not normally interact with each other, but which each interact with a third molecule so that, in the presence of the third molecule, the putative binding partners are brought together. Thus, substances which influence an interaction between putative binding partners include those which stimulate a weak interaction between putative binding partners, as well as one or more molecules which mediate interaction between molecules which do not normally interact with each other. In addition, substances which influence an interaction between putative binding partners can include those which directly or indirectly affect an upstream event which results in association between the putative binding partners. For example, if phosphorylation of one of the putative binding partners endows it with the capacity to associate with another of the putative binding partners; substances which influence the interaction of the putative binding partners include those which directly or indirectly affect a kinase activity.

Assays can be developed as disclosed herein to examine the effect on intermolecular interactions of a variety of compositions including drugs such as antipyretic and anti-inflammatory drugs, analgesics, antiarthritics, antispasmodics, antidepressants, antipsychotics, tranquilizers, antianxiety drugs, narcotic antagonists, antiparkinsonism agents, cholinergic antagonists, chemotherapeutic agents, immunosuppressive agents, antiviral agents, parasiticides, appetite suppressants, antiemetics, antihistamines, antimigraine agents, coronary vasodilators, cerebral vasodilators, peripheral vasodilators, hormonal agents, contraceptives, antithrombotic agents, diuretics, antihypertensive agents, cardiovascular drugs, opioids, and vitamins.

Protein-protein interactions mediated by a third molecule can be detected and quantitated. The kinetics of binding also can be studied. An example of such a system is described in Examples 1 and 2 below, wherein β-gal fusion proteins are used to monitor the rapamycin-mediated interaction of the FKBP12 and FRAP proteins. Belshaw, P. J. et al., *Proc. Natl. Acad. Sci. USA*, 93: 4604–4607 (1996); Brown et al., *Nature* 369: 756–758 (1994); Chen, et al., *Proc. Natl. Acad. Sci., USA*, 92:4947–4951 (1995); and Choi, J. et al., *Science*, 273:239–242 (1996). For example, kinetics of binding can be determined by measuring β-gal activity at different times following addition of rapamycin to cultures of cells expressing fusions of FKBP12 and FRAP to two complementing, low affinity β-gal mutants (e.g., Δα and Δω). A dose-response curve can also be obtained, in which the extent of binding, as measured by β-gal activity, is determined as a function of rapamycin concentration.

This assay can be adapted to control for the possible effect of a protein component on its fusion partner, thereby enabling the study of protein-protein interactions in a quantitative fashion. In one such control system, tripartite fusion constructs including a reporter subunit, a binding protein and the protein of interest are provided. As described below in Example 3, in one embodiment, the fusion protein includes 1) a β-gal mutant portion, 2) a FKBP12 or FRAP portion, and 3) a test protein portion. The most N-terminal component is the test protein, followed by FKBP12-Δω or FRAP-Δα. The presence of FKBP12 and FRAP in these constructs allows rapamycin-mediated dimerization of the fusion proteins. The absolute values of β-gal activity obtained by simple co-expression of a fusion containing a test protein of interest and fusions containing different potential interacting partners is determined. In parallel samples, β-gal activity is measured upon induction of complementation with a fixed amount of rapamycin. The ratio of β-gal activity obtained in the absence and the presence of rapamycin indicates the relative abilities of the different protein pairs to interact with each other.

A further advantage of the tripartite fusion system is that the presence of the FKBP12 and FRAP components provides a flexible hinge domain between the β-gal mutants and the test protein. This reduces the possibility of interference between the β-gal component and the test protein. Furthermore, it allows direct testing of the functional integrity of the β-gal components in the fusions without the need for recloning into more efficient viral vectors. For example, the tetracycline repressor, tetR, forms homodimers in mammalian cells with high efficiency. Hinrichs et al. (1994) *Science* 264:418–420. Coexpression of tetR-FKBP12-Δω and tetR-FRAP-Δα fusions yielded β-gal-positive cells, as shown in Example 3, showing that it is possible to construct functional tripartite fusions, in which dimerization of the N-terminal peptide component efficiently drives complementation of the C-terminal mutant β-gal polypeptides, with the FKBP12 and FRAP components serving as both internal standards and flexible hinges.

The system may be further tested and compared by constructing fusions between each β-gal mutant and the complete coding sequence of MEF2c. Since MEF2c is known to form homodimers in vivo, coexpression of both β-gal mutants fused to MEF2c should result in readily detectable enzymatic activity. MEF2c mutants that are impaired in their dimerization potential are available and fusion of one of the mutants to one of the β-gal mutants can serve as a negative control to further validate the system. Molkentin, et al., *Mol. Cell. Biol.*, 16:2627–2636 (1996).

The reporter system can also be designed with controls to permit the quantitation of the expression level of the β-gal fusion proteins. This will make it possible to control for potential differential expression of the two (or more) fusion proteins. For example, a peptide tag for which well-characterized monoclonal antibodies are available may be fused in frame at the C-terminus of each β-gal mutant. Different tags, such as flag and myc may be used for Δα and Δω, to allow differential detection of the two mutants even when coexpressed in the same cells. In parallel with the determination of β-gal activity in the lysates of these cells, an ELISA assay can determine the precise amount of each β-gal fusion protein in the same lysates. First, a polyclonal anti-β-gal antiserum may be used to immobilize the antigens. Then the monoclonal antibody directed against the appropriate tag followed by an enzyme-linked anti-mouse secondary antibody may be used to quantify the amount of the β-gal fusion protein of interest. Such an approach, employing well-characterized techniques, should allow a determination of the expression levels of each fusion protein. This modification will be useful where the attached tag does not impair the binding of the protein or the ability of the reporter subunits to complement.

APPLICATIONS OF THE INVENTION

As will be apparent to one of skill in the art, the invention allows, for the first time, a broad range of studies of multiprotein and other types of multi-molecular interaction to be carried out quantitatively or qualitatively in living cells. In what follows, non-limiting examples of different applications of the invention are provided.

The observation that levels of β-gal activity in the presence and absence of forced complementation can be distinguished, both biochemically (FIG. 5) and by FACS (Example 10 and FIG. 6), suggests that the methods of the invention can be used to screen for new binding partner(s) for a given target protein. In this embodiment, the target protein, fused to a weakly-complementing β-gal mutant is stably expressed in a well-characterized cell line. Expression libraries containing cDNAs fused to a weakly-complementing β-gal mutant are introduced into these cells using, for example, retroviral vectors (e.g., Kitamura et al., *Proc Natl. Acad. Sci. USA* 92:9146–9150 (1995) ) or any other means of gene transfer known in the art. Vectors expressing gene products that interact with the target protein are isolated by identifying β-gal-positive clones. An advantage of this system is that the screen can be carried out in any cell type, regardless of the cell's milieu of endogenous (and potentially competing) proteins. A further possibility for this type of system is that the target protein can be localized to a specific cellular compartment, with the aim of identifying proteins involved in interactions restricted to that particular location.

The use of fluorescence-activated cell sorting techniques is particularly well-suited to this embodiment of the invention. For example, β-gal-positive cells which contain cDNAs expressing gene products that interact with the target protein will generate a signal that will allow such cells to be purified by cell-sorting techniques. Such cDNAs could be delivered, for example, using retroviral vectors that allow introduction of high complexity cDNA libraries with high infection efficiency.

The assays and methods of the invention can also be carried out in the presence of extracellular signaling molecules, growth factors or differentiation factors, peptides, drugs or synthetic analogs, or the like, whose presence or effects might alter the potential for interaction between two or more given proteins in a particular cell type.

Figure 7A:
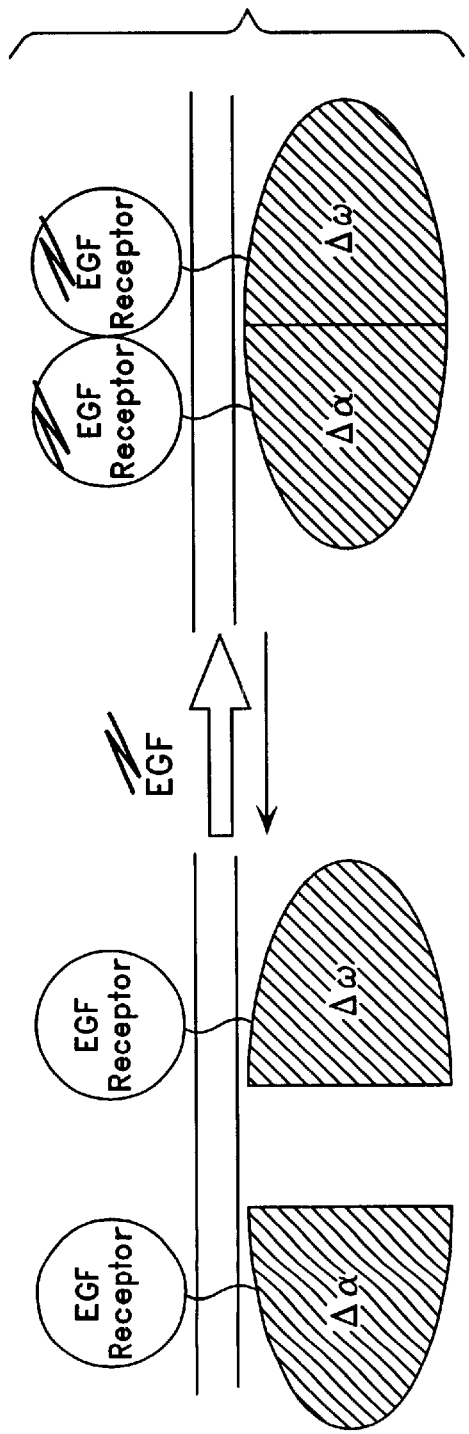
FIGS. 7A–7F show EGF receptor dimerization monitored using β-gal complementation.

Detection of molecular interactions, using the methods and compositions of the invention, is not limited to those occurring in the nucleus, nor is it limited to intracellular interactions. For instance, interactions involving surface receptors can be detected in the practice of the invention. In one embodiment, the invention provides new techniques for detecting ligand-induced dimerization of surface receptors in living cells. Dimerization, or higher order oligomerization, of cell surface receptors is often a prerequisite for receptor activation and ensuing signal transduction. For example, the binding of epidermal growth factor (EGF) to its receptor stabilizes the dimerization of the receptor and leads to activation of its tyrosine kinase activity. Schlessinger et al. (1992) *Neuron* 9:383–391; Ullrich et al. (1990) *Cell* 61:203–212; and Weiss et al (1997) *Curr. Opin. Genet. Dev.* 7:80–86. Example 11, infra, discloses the use of β-gal complementation to monitor membrane receptor dimerization in living cells. For this purpose, the weakly complementing Δα and Δω deletion mutants of β-gal were fused to the extracellular and transmembrane regions of the human EGF receptor to form a chimeric receptor molecule (see FIG. 7A). Deletion of the cytoplasmic domain of the receptor prevents the internalization and degradation of the receptor that is normally observed following EGF stimulation of cells (Livneh et al. (1986) *J. Biol. Chem.* 261:12490–12497), permitting an analysis of receptor dimerization over time in changing conditions. The results presented in Example 11 demonstrate that this embodiment of the invention can be used to detect a previously-unrecognized mode of regulation of EGF receptor signaling, in which EGF receptor tyrosine kinase activity acts as a feedback inhibitor limiting the dimerization of the receptor.

The practice of the invention is not limited to detection of interaction between two different molecules. Multimerization of a molecule can also be detected using the methods and compositions of the invention. In this regard, Example 11 discloses the detection of receptor dimerization through the practice of the invention.

By combining the methods and compositions of the invention with state-of-the-art methods for construction of high-titer, high-complexity cDNA libraries in retroviruses (e.g., Pear et al., (1993) *Proc. Natl. Acad. Sci. USA* 90:8392–8396), it will be possible to identify interaction partners of a specific test protein in mammalian cells (i.e., perform functional genomics at the protein level). For this application, construction of cDNA libraries in retroviral vectors wherein the cDNA coding sequence is fused to a sequence encoding a low affinity reporter subunit will be used. A sequence encoding a binding protein of interest will be fused to a low affinity reporter subunit in a first retroviral vector. In a second series of retroviral vectors, a second complementing low affinity reporter subunit will be fused to a variety of different proteins that will be tested for their ability to bind to the protein of interest. Testing will be conducted by co-infection of cells with the first and one of the series of second retroviral vectors. Those test proteins which are capable of binding to the protein of interest will allow detection of a reporter signal in cells in which they are co-expressed with the protein of interest. This application will also be useful in screening for agonists and antagonists of medically-relevant protein interactions.

In one embodiment of the invention, cells in which a protein encoded by one of the series of second vectors is able to interact with the binding protein of interest encoded by the first vector are detected and isolated by flow cytometry or fluorescence-activated cell sorting (FACS). Methods for flow cytometry and FACS are well-known in the art; e.g., Nolan et al. (1988) *Proc. Natl. Acad. Sci USA* 85:2603–2607; Webster et al., *Exp. Cell Research,* 174:252–265 (1988); and Parks et al. (1986) in *The Handbook of Experimental Immunology*, (eds. Weir, D. M., Herzenberg, L. A., Blackwell, C. C. & Herzenberg, L. A.), Blackwell, Edinburgh, 4th edition, pp. 29.1–29.21. In this way, clones of cells in which binding occurs can be isolated and propagated for further study. This aspect is particularly suited for studies of developmental mechanisms, wherein it is possible to select a population of cells in which a particular developmentally-relevant interaction has occurred and study the further development of that cell population, while at the same time, studying the further development of cells in which the interaction has not occurred, for comparison. In a similar fashion, the practice of the invention makes it possible to isolate and/or study the further development of cells exhibiting interactions involving protein such as transcriptional regulatory proteins, translational regulatory proteins, DNA replication proteins, mRNA splicing proteins, proteins involved in signal transduction, proteins involved in cell-cell and cell-substrate adhesion (for example, cell movement, axon guidance and angiogenesis), oncogene products, tumor suppressors, proteins involved in cell-cycle control and viral proteins, such as those involved in regulation of viral replication, virus-host interactions and virus assembly, and proteins which are subunits, crosslinkers, modifying agents or molecular motors within the cytoskeleton of cells.

For a given target protein whose gene is capable of being fused to a low-affinity complementing reporter subunit, it is possible to identify known and heretofore unknown proteins or other endogenous or extraneous substances with which it interacts, by using the compositions and methods of the invention. In like manner, for a sequence which encodes a protein of unknown function, such as may be obtained from a nucleic acid sequence database, (or a plurality of sequences such as a cDNA library) the practice of the invention allows one to identify molecules with which the encoded protein interacts. The identity of the interacting molecule(s) is likely to provide information with respect to the structure and/or function of the unknown protein. Thus, the practice of the invention will likely aid in the identification and characterization of newly-discovered proteins and protein-coding nucleic acid sequences.

In another aspect of the invention, a shotgun approach to the identification of protein-protein interactions can be taken by generating a first set of constructs which will express the encoded products of one cDNA library fused to a first low-affinity complementing subunit and a second set of constructs which will express the encoded products of a second (or the same) cDNA library, fused to a second low-affinity complementing subunit. Co-expression of the two sets of constructs and selection of cells in which complementation occurs will allow the isolation of clones and the identification of cDNAs which encode interacting partners. One or both of the interacting partners may be known; alternatively, both of the interacting partners may represent heretofore unidentified proteins. If both partners are known, new information about their binding specificity may be obtained. If one partner is known, it may provide information on the function of the unknown binding partner. If neither are known, the observation that they interact may assist in the eventual identification of one or both of the interacting pair.

The invention may be applied to studies of the mechanisms that regulate either homo- or hetero-dimerization or multimerization of specific molecules, including high efficiency screening to identify synthetic or naturally occurring compounds capable of influencing such dimerization.

The invention can be used for investigations relating to the localization of specific complexes within intact cells, or intact animals. Types of cells which can be used are primary or established cell lines and other types of embryonic, neonatal or adult cells, or transformed cells (for example, spontaneously- or virally-transformed). These include, but are not limited to fibroblasts, macrophages, myoblasts, osteoclasts, osteoblasts, hematopoietic cells, neurons, glial cells, primary B- and T-cells, B- and T-cell lines, chondrocytes, keratinocytes, adipocytes and hepatocytes.

It is also possible, through practice of the invention, to devise systems for regulation of enzyme activity by regulating the association of complementing mutants. This aspect of the invention has potential applications to human therapy, as a method to regulate the enzyme-driven conversion of pro-drugs into their active forms.

Processes involving molecular interactions, particularly protein-protein interactions, which can be studied in the practice of the invention include, but are not limited to, transcription, translation, replication, mitosis, growth control, progression and regulation of the cell-cycle, apoptosis, cell-cell, cell-substratum and cell-ligand interactions, intracellular signal transduction cascades, oncogenesis, cell lineages, and embryonic development. Examples of cell ligands include leptin and growth factors such as epidermal growth factor (EGF), nerve growth factor (NGF), platelet-derived growth factor (PDGF), and insulin-like growth factors I and II (IGF-I and IGF-II), transforming growth factors α and β (TGF-α and TGF-β), endorphins and endorphin receptors, prostaglandins and their receptors, cytokines and their receptors, neurotransmitters and their receptors, adrenergic receptors, and cholinergic receptors. Receptors which could interact with ligands include EGF, NGF, and PDGF receptors and leptin receptors. Analysis of EGF receptor dimerization, using the methods and compositions of the invention, is provided in Example 11, infra.

Additional interactions that can be studied by the practice of the invention include interactions involved in cell metabolism and cell structure. These include, but are not limited to, interactions that are involved in energy metabolism or which establish or modify the structure of the membranes, cytoplasm, cytoskeleton, organelles, nuclei, nuclear matrix or chromosomes of cells. Interactions among constituents of the extracellular matrix, or between constituents of the extracellular matrix and cells, can also be studied with the methods and compositions of the invention.

The invention will be further understood by the following non-limiting examples.

EXAMPLES

Example 1
Preparation and Transfection of Retroviral Construct Encoding a β-Galactosidase Reporter System A reporter system using β-galactosidase ("β-gal") complementation to evaluate protein-protein interactions was constructed. A well-characterized protein complex developed by Schreiber was used as a test system to provide the protein binding moieties. Belshaw, P. J. et al., *Proc. Natl. Acad. Sci. USA*, 93: 4604–4607 (1996); Brown et al., *Nature* 369: 756–758 (1994); Chen, et al, *Proc. Natl Acad Sci., USA*, 92:4947–4951 (1995); and Choi, J. et al., *Science*, 273:239–242 (1996), the disclosures of which are incorporated herein. In this protein complex, the intracellular rapamycin binding protein, FK506-binding protein-12 (FKBP12), interacts with intracellular FKBP-rapamycin associated protein (FRAP) only when rapamycin is present in the culture medium, an interaction that increases with the dose of rapamycin. Rapamycin is a small, cell-permeable molecule that binds to the two intracellular proteins via independent determinants. Since rapamycin is unable to bind two FKBP12 molecules at the same time and FRAP only binds rapamycin within the FKBP12-rapamycin complex, only heterodimers should form upon rapamycin treatment. Ho, S. N. et al., *Nature*, 382:822–826 (1996), the disclosure of which is incorporated herein.

The β-gal system was combined with the FKBP12/FRAP/rapamycin system as follows. Two different retroviral constructs were produced, each encoding fusion proteins of the Δω or Δα β-gal mutants, and either FKBP12 or the FKBP-rapamycin binding domain of FRAP, respectively (FKBP12-Δω and FRAP-Δα).

The Δα or Δω β-gal mutants were obtained as described in Mohler and Blau, *Proc. Natl. Acad. Sci.*, 93:12423–12427 (1996), the disclosure of which is incorporated herein.

To fuse the sequences coding for FKBP12 and the FKBP12-rapamycin binding domain in frame with legal, an adapter oligonucleotide (CATGGAGCTCGAGAG(SEQ ID NO:1)) containing an XhoI site was inserted in the NcoI site at the ATG of the Δα and Δω β-gal mutants described by Mohler and Blau, supra. Two XhoI-SalI DNA fragments corresponding to amino acids 2025–2114 of human FRAP and to the complete coding sequence of human FKBP12 were cloned in the XhoI site of the modified Δα and Δω mutants, generating FRAP-Δα and FKBP12-Δω. Conservation of the appropriate reading frame was confirmed by sequencing for both constructs.

To insert the FRAP-Δα and FKBP12-Δω coding sequences in the pWZL-Neo and pWZL-Hygro retroviruses, an adapter oligonucleotide containing NcoI and BamHI sites (GATCACCATGGACGCGTGGATCCC(SEQ ID NO:2)) was inserted in the BamhI and XhoI sites of the pWZL vectors. Both the original sites were destroyed by this insertion. The FRAP-Δα and FKBP12-Δω coding sequences were then inserted in the modified pWZL vectors as NcoI-BamHI fragments.

The cDNAs encoding FKBP12-Δω and FRAP-Δα were inserted into a mouse ecotropic retroviral vector upstream of the hygromycin resistance or neomycin resistance genes, respectively, as described above. By using an Encephalomyocarditis virus internal ribosomal entry sequence (IRES), introduction of a single retroviral vector ensured production of a bicistronic mRNA and translation of both the Δα-β-gal-FRAP-protein and the drug selectable hygromycin protein. A second retroviral vector yielded the Δω-β-gal-FKBP12 protein and neomycin resistance protein.

For virus production and infection, proviral constructs were introduced into packaging cells by calcium phosphate transfection. The supernatant media containing retrovirus from the packaging cells was harvested 24 to 72 hours after transfection and used to infect C2C12 cells in the presence of 8 μg/mL polybrene. Singly and doubly infected cells were selected with the appropriate drugs. Both Geneticin and Hygromycin were used at a final concentration of 1 mg/ml. The selected cells were expanded as populations for subsequent experiments.

Although the background β-gal detected with the Δα and Δω mutants expressed from MFG retroviral vectors described previously (Dhawan et al., *Science*, 254:1509–1512 (1991) was relatively low (Mohler, W. A., & Blau, H. M., *Proc. Natl. Acad. Sci. USA*, 93:12423–12427 (1996), the disclosure of which is incorporated herein), it was further reduced by using retroviral vectors with point mutations that deleted the splice donor/acceptor sequences upstream of the β-gal ATG (pWZL). These mutations result in a lower translation efficiency of the first coding sequence contained in the vector, but do not affect the expression of the selectable marker, which is solely dependent on the IRES. Using this vector, two-fold less of the upstream protein was expressed compared to vectors containing the same LTRs (long terminal repeats) and the wild-type splice donor/acceptor sequences. Such a reduction in translation reduces the concentration of the fusion protein and consequent spontaneous interactions of β-gal mutants irrespective of the test proteins to which they are fused. As a result, in preliminary experiments, the background enzyme activity measured by luminometer for Δα and Δω β-gal mutants alone was reduced from low to essentially undetectable.

Infectious viral particles were produced by transient transfection of each construct shown in FIG. 2a into a packaging cell line modified from that described by Pear et al., (1993) *Proc. Natl. Acad. Sci. USA* 90:8392–8396 by calcium phosphate transfection. The supernatant media containing retrovirus from the packaging cells was harvested 24 to 72 hours after transfection and used to infect C2C12 cells in the presence of 8 μg/mL polybrene. C2C12 myoblasts were infected either singly with each retrovirus alone or simultaneously with both. All experiments were performed after selection with hygromycin and G418 to ensure that 100% of the cells contained both constructs. Both Geneticin and hygromycin were used at a final concentration of 1mg/ml. The selected cells were expanded as populations for subsequent experiments.

Example 2
Assays of Binding and Activity of the β-Galactosidase Reporter System

Figure 3B:
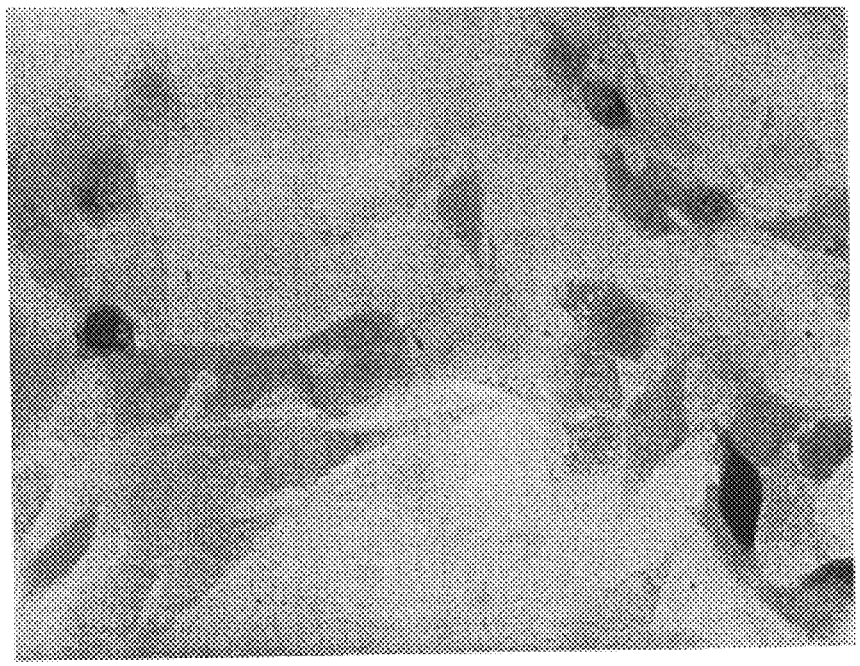

Following the addition of rapamycin to the media, the transfected cells obtained as described in Example 1 were assayed for β-gal activity. As shown in FIG. 3, C2C12cells expressing both FKBP12-Δω and FRAP-Δα were tested by exposure to 10 ng/ml rapamycin (FIG. 3b) for 12 hr or to no drug at all (FIG. 3a). Only those cells expressing both constructs exhibited β-gal activity, readily visualized by X-gal staining of fixed cells (FIG. 3b). It is advantageous that cytoplasmic staining is detectable with this method, in contrast to prior methods such as the yeast two-hybrid system, which report only nuclear interactions. X-gal staining was conducted as follows: Cells were fixed 5 minutes in PBS plus 4% paraformaldehyde and rinsed in PBS prior to staining. Indigogenic X-gal staining was performed overnight at 37° C. in PBS plus 1 mg/mL X-gal, 1 mM $MgCl_2$, 5 mM $K_3Fe(CN)_6$, 5 mM $K_4Fe(CN)_6$.

The kinetics of activation of β-gal upon rapamycin treatment were determined. C2C12 cells expressing both fusion proteins were plated in replicate in 96 well plates. Rapamycin was added to the culture medium, and the β-gal activity measured at different time points. For each time point, six replicate samples were assayed with a sensitive chemiluminescence assay, as described in Mohler, W. A., & Blau, H. M., *Proc. Natl. Acad. Sci., USA*, 93:12423–12427 (1996), the disclosure of which is incorporated herein. In the assay, cells cultured in microtiter plates were lysed in situ in 50 μL of a 1:3 mixture of lysis and assay buffers containing Galacton Plus substrate from the Galactolight Plus assay kit (Tropix, Bedford, Mass.). Reactions proceeded for 1 hour at room temperature. After addition of Light Emission Accelerator solution, luminescence was measured in a scintillation counter.

The results, shown in FIG. 4, indicate that the interaction assays for the fusion proteins are specific, and exhibit similar kinetics and a comparable dose-response curve to assays of the FKBP12/FRAP/rapamycin protein complex alone. Ho, S. N. et al., *Nature*, 382:822–826 (1996). Rapamycin induced a 30-fold increase in β-gal activity within 5 hours. As a control, no rapamycin was added, and no β-gal activity was detected above background. As a second control, in cell populations expressing only one of the two constructs, β-gal activity did not increase above background when rapamycin was added.

In FIG. 4b, the dose response curve is shown. The activation of β-gal was dependent on the dose of rapamycin, which appeared linear over a range of 0 to 10 ng/ml of the drug. This linearity provides support that β-gal enzymatic activity can serve as a reporter to quantitate protein-protein interactions. The close approximation of both the dose response and the kinetics to that observed by others (Ho, S. N. et al., *Nature*, 382:822–826 (1996)) suggests that the fusion to β-gal peptides is not interfering with the interaction of the FKBP12 and FRAP proteins. Moreover, endogenous FKBP12 and FRAP proteins are ubiquitously expressed and are capable of interacting with each other or with the fusion proteins in the presence of rapamycin, without generating β-gal activity. Detection of β-gal activity, as shown above, indicates that productive FRAP-Δα and FKBP12-Δω dimers will form in a cellular environment containing competing endogenous proteins, and that the resultant β-gal activity reflects the interaction of FRAP and FKBP12-rapamycin Thus, the β-gal fusion proteins can be used to monitor the interaction of proteins in the FKBP12/FRAP/rapamycin complex and in other types of multiprotein complexes.

Figure 5:
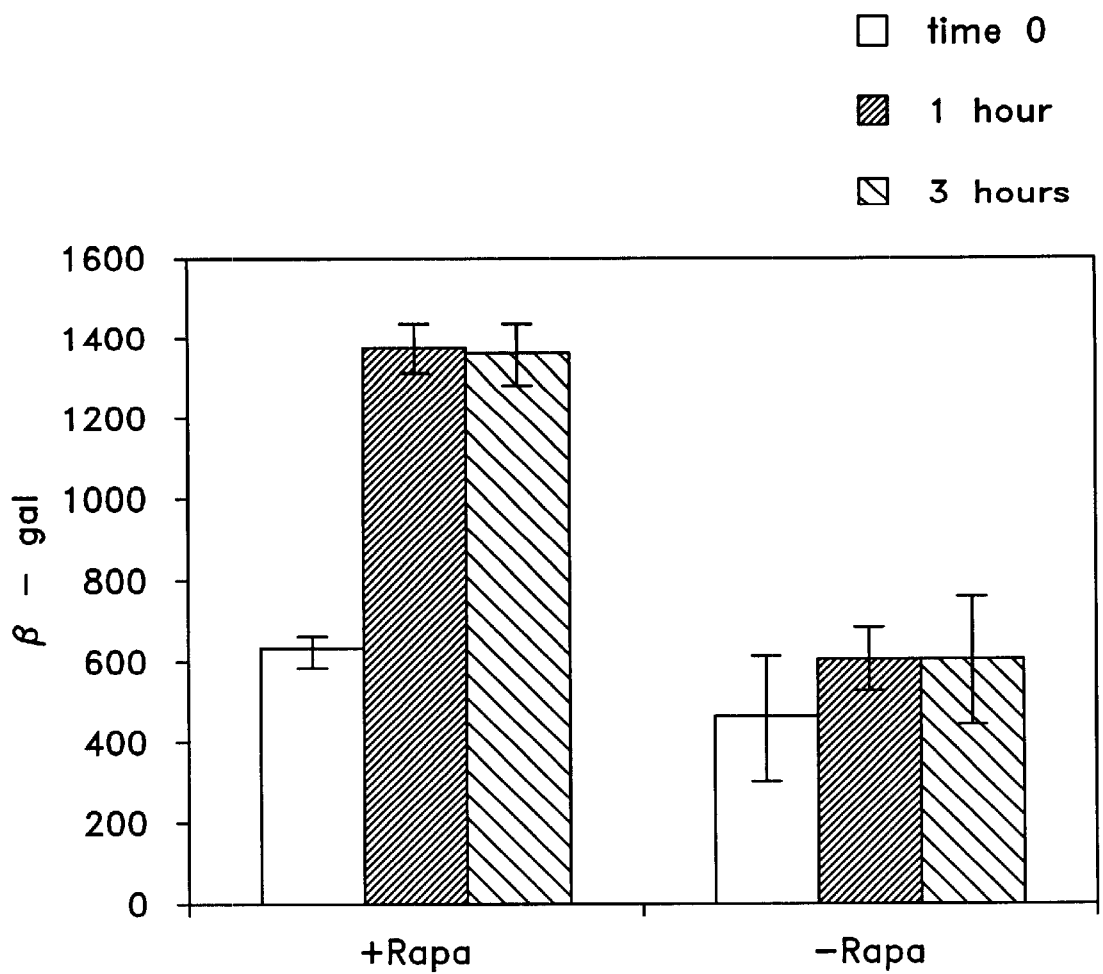
FIG. 5 shows rapamycin-dependent increase in β-gal activity in lysates from cells expressing both FKBP12-Δω and FRAP-Δα fusion proteins, measured by chemiluminescence.
Figure 6:
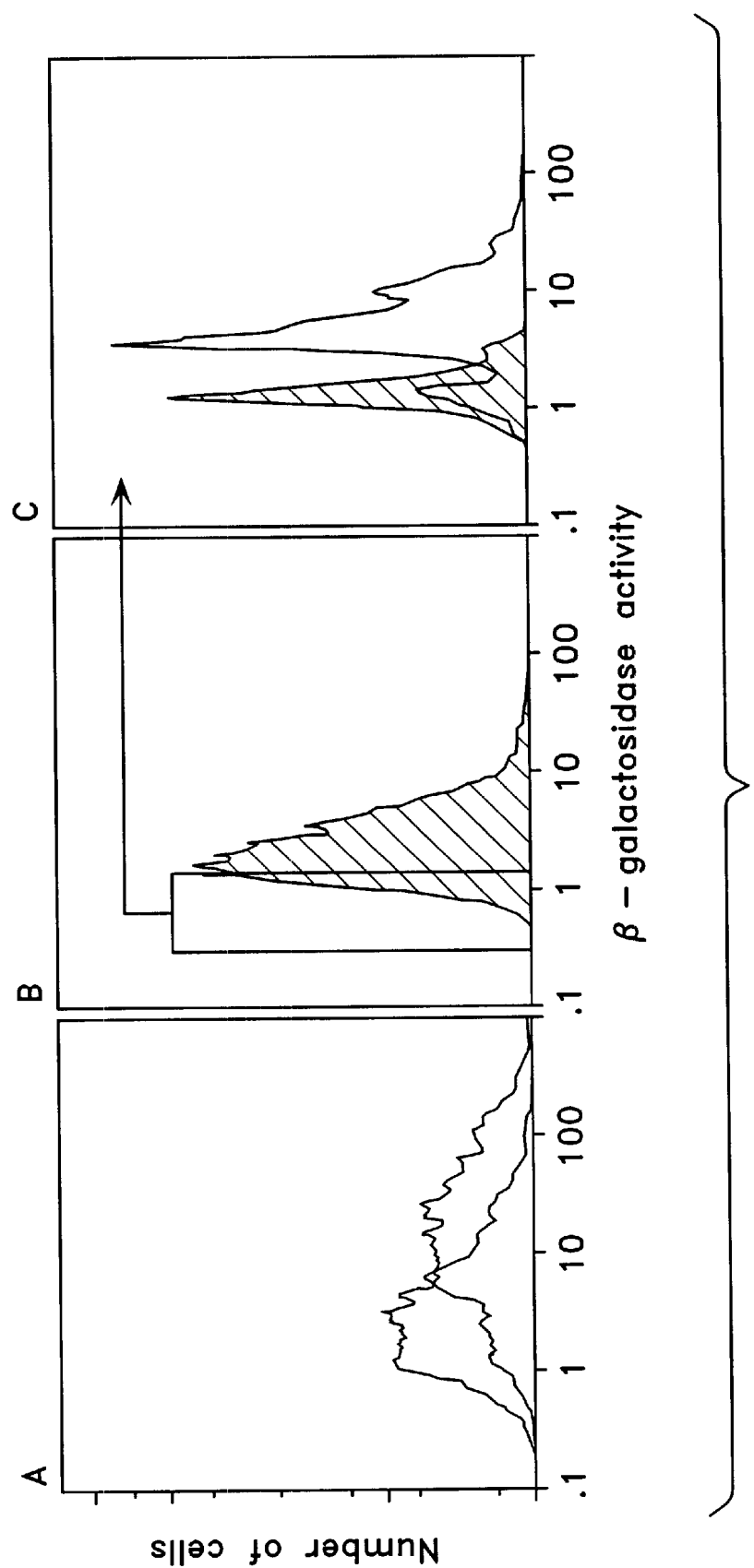
FIG. 6A shows analysis by Fluorescence-Activated Cell Sorting (FACS) of C2C12 cells expressing both FKBP12-Δω and FRAP-Δα after 90 minutes of rapamycin treatment. Dark peaks represent profiles obtained from untreated samples; light peaks represent profiles from samples that have been treated with 10 ng/ml rapamycin.
FIG. 6B shows a FACS profile of untreated cells and indicates a subpopulation selected on the basis of low β-gal activity.
FIG. 6C shows FACS analysis of the subpopulation of cells selected in FIG. 6B after overnight culture in the absence (dark peak) or presence (light peak) of rapamycin.

It is also possible to detect and quantitate binding activity in cell lysates. As shown in FIG. 5, cells expressing both FKBP12-Δω and FRAP-Δα fusion proteins were expanded in the absence of rapamycin and lysed. 100 ng/ml rapamycin was added to half of the samples, and the β-gal activity in the treated and untreated lysates was determined immediately (white bar), after one hour (black bar) or after 3 hours (gray bar). A greater than two-fold increase in β-gal activity was observed in the rapamycin-treated lysates one hour after administration of the drug. In control lysates that were not exposed to rapamycin, no statistically significant increase in β-gal activity was detected. The ability to detect and quantitate protein-protein interactions in cell lysates using the methods and compositions of the invention indicates that interactions between mature, fully-folded proteins can be detected and quantitated; co-translational assembly of complexes in not required for formation of complexes that can be monitored by β-gal activity.

Example 3
Tripartite Fusions For the Quantitation of Protein-protein Interactions To permit protein interactions to be studied in a quantitative manner in the system described in the above Examples and to control for effects on either the binding ability of the binding moiety or the complementing ability of the reporter subunits resulting from both activities being present in a single fusion protein, additional modifications were made to monitor the expression of the components of the system. In the above described system, the β-gal fusion proteins will be expressed from the same viral promoter, however, for some proteins, it is possible that their expression level will be influenced by the specific fusion partner. In particular, some proteins or domains could affect the stability or conformation of the β-gal domain. As a result, differences in the ability of the test proteins (the putative binding moieties) to complement one another could be observed that are not based on a physiological mechanism.

In order to avoid these problems, fusions containing three components (β-gal mutant, FKBP12 or FRAP, and the test protein) were constructed. The most N-terminal component is the test protein, followed by FKBP12-Δω or FRAP-Δα (see the exemplary system in FIG. 2b, where the test protein portions of the fusion are indicated by X and X'). The presence of the FKBP12 and FRAP portions allows rapamycin-mediated dimerization of these fusions, and the efficiency of β-gal complementation in the presence of rapamycin appears to be dependent on the FKBP12/FRAP/rapamycin interaction. The absolute values of β-gal activity obtained by simple coexpression (in the absence of rapamycin) of fusions containing a fixed protein of interest and different interacting partners was determined. In parallel fixed amount of rapamycin. The ratio between the β-gal activity obtained in the absence or in the presence of rapamycin indicated the relative ability of the different protein pairs to interact with each other. An added advantage of this approach is that the presence of the FKBP12 and FRAP domains provide a flexible hinge between the β-gal mutants and the putative binding moieties that are being analyzed. This reduces the possibility of interference between β-gal and the proteins of interest. Furthermore, it allows direct testing of the functional integrity of the β-gal components in the fusions without the need for recloning into more efficient viral vectors.

Results were obtained with tetR-FKBP12-Δω or tetR-FRAP-Δα tripartite fusions (see example in FIG. 2b). Coexpression of these constructs, in which dimerization is driven by the tetracycline repressor (tetR) protein (Hinrichs, W. et al., Science, 264:418–420 (1994), the disclosure of which is incorporated herein), readily yielded β-gal positive cells. This indicates that functional tripartite fusions can be constructed, in which the dimerization of the most N-terminal peptide component efficiently drives complementation of the C-terminal β-gal deletion mutant polypeptides.

Example 4
Dimerization of Myogenic Regulators Using Complementing β-gal Fusion Proteins The β-gal complementation system is used to assay for the dimerization and nuclear translocation of HLH proteins (helix-loop-helix proteins, Murre et al. (1989) Cell 56:777–783) including activators of muscle-specific proteins (myoD, myogenin, myf5, MRF-4), inhibitors of myogenesis (Id, Mtwist, I-mf) and ubiquitous E2A-type proteins (E47, E12, HEB).

In a first step, a myoD-Δα-β-gal (myoD-Δα) fusion construct and a E12-Δω-β-gal (E12-Δω) fusion construct are engineered in selectable retroviral vectors, as described above for FRAP-Δα and FKBP12-Δω. The two constructs are transduced into C2C12 myoblasts. Following selection with the appropriate drugs for cells which express both constructs, β-gal activity is quantitated using the chemiluminescent assay described above. β-gal activity indicates that heterodimerization of the fusion proteins is occurring in this cell type. If β-gal activity is detected, individual cells are analyzed using a fluorescent X-gal stain in order to determine if the heterodimers are present in the nucleus. Since wild-type β-gal can be specifically directed to and detected in the nucleus by inclusion of a nuclear localization sequence (nls) (Hughes and Blau, Nature, 345:350–352 (1990)), activity from the β-gal hybrid protein may be detected in the nucleus. Knowledge of the site of localization in the cytoplasm or nucleus will aid in assessing the function of the protein interactions, e.g. sequestration and inhibiting activity, or promoting activity. This method permits visualization of fluorescent markers of myogenesis, such as desmin, and creatine kinase, in correlation with the localization of β-gal, using the sensitive Fluor-X-Gal substrate described above (Mohler, W. A., & Blau, H. M., Proc. Natl. Acad. Sci., USA, 93:12423–12427 (1996)).

All fusion constructs between myogenic regulators and complementing β-gal mutants described in the following sections may be tested in a muscle cell where heterodimerization of the endogenous myogenic regulator is known to occur. In addition, the following controls also may be performed. The myoD-Δα construct may be contransduced into the cell with FKBP12-Δω and the E12-Δω construct may be cotransduced with FRAP-Δα. This combination of constructs should result in no β-gal activity, unless some unusual mechanism exists in the particular cell type being tested that enhances complementation of the weakly complementing β-gal peptides independent of heterodimerization of the non-β-gal parts of the molecule. The FRAP-Δα and FKBP12-Δω may also be cotransduced and cells treated with rapamycin as a positive control for complementation in each cell type. Cells in high serum medium (growth medium) and cells in low serum medium (differentiation medium) should/will give different results.

Example 5
In vivo Assay For the Effect of Growth Factors and Substrates on Heterodimerization and Homodimerization Using the constructs described above in Example 4, C2C12 myoblasts are transduced with one of the myogenic HLH fusion constructs and the E12-Δω construct. Although C2C12 cells will already contain endogenous myogenic HLH proteins and E12, the chimeric constructs will act as a "tracer" to measure the extent of heterodimerization. Transduced cells then may be stimulated to either differentiate or proliferate by changes in serum levels or the addition of growth factors (TGF-β, bFGF, IGF-I and IGF-II) in the presence or absence of substrates such as fibronectin or laminin. β-gal activity then is measured as a function of time. Rapid changes in β-gal activity after growth factor stimulation may suggest a more direct mechanism of action of a given extracellular signal on the formation of specific heterodimers. Slower changes may indicate that the extracellular signal acts indirectly, for example by up-regulating the expression of a competing factor which can sequester one or both fusion proteins. Changes in β-gal activity may be correlated with the expression levels of known inhibitors of differentiation such as Id proteins, measured by Northern blot in parallel samples. A comparison of the kinetics of changes in β-gal activity obtained with each pair of test proteins in parallel experiments will indicate whether specific MRFs (muscle regulatory factors, Yun et al. (1996) Curr. Opin. Cell Biol. 8:877–879; and Cossu et al (1996) Trends Genet., 12:218–223) or inhibitors differ in their ability to respond to extracellular signals. When a growth factor or substrate capable of influencing heterodimer formation (or nuclear translocation) is identified, the experiments are repeated in other, non-myogenic cell types. The analysis of the effect of a specific growth factor in different cell types indicates whether the intracellular components of the corresponding signal transduction pathway are tissue-specific.

These studies in tissue culture cells permit the relative affinity and compartmentalization of specific protein partners under conditions of growth and differentiation, and subsequently in response to known signal transducers, to be evaluated. The interactions of these factors may be tested in a relevant physiological background in competition with the prevalent endogenous components present in the cell at the time. Most analyses of the interactions of myogenic factors performed thus far have been carried out in vitro, in purified systems, or in yeast (Benezra et al., Cell, 61:1213–1230 (1990); Lassar et al., Cell, 66:305–315 (1991); Hu et al., Mol. Cell. Biol., 12:1031–1042 (1992); Chenetal., Cell, 86:731–741 (1996); and Spicer et al., Science, 272:1476–1480 (1996). The relatively low sensitivity of the biochemical methods used to directly detect interactions in mammalian cells, such as immunoprecipitation or activation of a reporter gene construct, required high levels of protein and overexpression of the construct, usually obtained by transient transfection, levels that could potentially force an interaction due to increased concentration. The methods disclosed herein permit protein-protein interactions that are functionally relevant at different points in the myogenic differentiation pathway to be studied. Clearly, the extracellular and intracellular milieu determines the stoichiometry and abundance of the these proteins at different times. As a result, competition of different proteins for the same dimerization partners, cofactors, and kinases or phosphatases in signal transduction pathways could have significant effects on which complexes actually form in intact cells. To assess the nature of such endogenous interactions, low expression levels are needed in order not to alter the levels inherent to the cell and characteristic of the "competitive" environment at a given time. Advantageously, high-level expression of the introduced proteins is not required in the systems described herein in order to assess the protein-protein interactions of interest. Indeed, by contrast with transient transfection assays or even most retroviral vectors with strong promoters and high translation efficiencies, the systems disclosed herein provide levels that should not perturb the natural endogenous physiological levels of the proposed test proteins in the cell.

Example 6
Analysis of Inhibitory and Myogenic HLH Proteins in Mice

The heterodimerization of inhibitory and myogenic HLH proteins in mice may be mapped. Mtwist and I-mf have been shown to inhibit myogenesis in mammalian tissue culture systems. In addition, they have been proposed to act via direct physical association with myogenic HLH proteins (Hebrok et al., Dev. Biol., 165:537–544 (1994); Rohwedel et al., Exp. Cell Res., 220:92–100 (1995); Chen et al., Cell, 86:731–741 (1996); Spicer et al., Science, 272:1476–1480 (1996)). During embryogenesis, Mtwist is expressed throughout the epithelial somite and is later excluded from the myotome (Fuchtbauer, Dev. Dyn., 204:316–322 (1995); and Stoetzel et al., Mech. Dev. 51:251–263 (1995)). Although I-mf expression has not been analyzed at early stages of somitogenesis, at 11.5 days post-coitum I-mf is highly expressed in the sclerotome but is excluded from the myotome (Chen et al, Cell, 86:731–741 (1996)). Thus, based on their expression domains in the embryo, these factors are thought to be critical for spatial and temporal restriction of the myogenic program in early development.

Further support for this hypothesis derives from analyses of myf5/lacZ embryos in which the myf5 coding region has been targeted and replaced by lacZ. Using β-gal as a marker of the myf5 expression pattern, cells expressing myf5 are detected in the presomitic mesoderm, where Mtwist is also expressed (Fuchtbauer, Dev. Dyn., 204:316–322 (1995); and Stoetzel et al., Mech. Dev. 51:251–263 (1995)), long before the onset of myogenesis (Cossu et al., Trends Genet., 12:218–223 (1996)). Later in development, myf5 and myoD are co-expressed together with Mtwist in the somite before the formation of a distinct myotome. Ott, et al., Development, 111: 1097–1107 (1991); Fuchtbauer, Dev. Dyn., 204:316–322 (1995); Stoetzel et al., Mech. Dev. 51:251–263 (1995); and Cossu et al., Trends Genet., 12:218–223 (1996)). These cells do not express other detectable myogenic markers (Ott, et al., 1991). Thus, the reporter systems disclosed herein may be used to determine if the myf5 and MyoD proteins in these cells are maintained in an inactive state by interaction with Mtwist and/or I-mf in heterodimers. At subsequent stages of development, Mtwist and I-mf are expressed in most of the non-myogenic mesoderm, where the expression of myogenic factors is excluded. Smith et al., J. Cell Biol., 127:95–105 (1994); Fuchtbauer, Dev. Dyn., 204:316–322 (1995); Stoetzel et al., Mech. Dev. 51:251–263 (1995); and Chen et al., Cell, 86:731–741 (1996). Possibly Mtwist and I-mf are involved in the creation of a sharp border between the myotome and the adjacent tissues at this stage.

The reporter systems disclosed herein permit detailed studies of the interactions between myogenic inhibitors and activators in vivo during embryonic development which can provide novel insights into the complex process of patterning during somitogenesis. Such studies are not limited to mice and can easily be performed in C. elegans, Drosophila, Xenopus, zebrafish and other experimental organisms. To date, a methodology that allows visualization of protein complexes in situ in the embryo has not been available. As a result, no definitive evidence is available as to when and where during embryonic development interactions of such HLH heterodimers might occur.

Example 7
Detection of HLH Heterodimers in Mouse Embryos

The β-gal complementation assay is well-suited for the detection of protein-protein interactions in vivo. Myf5-Δα, MyoD-Δα and Mtwist-Δω fusion proteins may be constructed. Mediation of β-gal complementation with these fusion proteins may be tested in the course of performing the experiments described above. Using well-established transgenic technology (Thomas and Capecchi, Nature, 324:34–38 (1986); and Capecchi, Science, 244: 1288–1292 (1989)), mouse lines may be generated in which one of the myf5, MyoD or Mtwist alleles has been replaced with the corresponding fusion protein. Thus myf5-Δα, MyoD-Δα and Mtwist-Δω fusion proteins will be expressed under the control of their endogenous promoters. The expression of the test protein can be verified in these mice. The Mtwist-Δω transgenic mouse may then be crossed with the myf5-Δα, and the MyoD-Δα transgenic mouse lines, and in each case the offspring may be analyzed in order to identify those carrying both of the fusion proteins. β-gal activity should only develop in those cells of the embryo in which Mtwist-Aco physically associates with the myf5-Δα or the MyoD-Δα fusion proteins. This analysis allows mapping when and where during embryonic development Mtwist is actually interacting with myf5 and MyoD to repress the myogenic phenotype.

Example 8
Targeting Strategy and Engineering of Necessary Constructs

The myf5-Δα fusion protein coding sequence may be inserted into the myf5 locus so that it will be expressed under the control of the endogenous myf5 regulatory elements. A similar insertion of wild type β-gal in the myf5 locus resulting in a fusion with the ATG of myf5 has been shown to reproduce faithfully the expression pattern of the endogenous gene. The targeting construct is based on the published myf5/lacZ targeting construct (Tajbakhsh and Buckingham, *Proc. Natl. Acad. Sci. USA*, 91:747–751 (1994); Tajbakhsh et al., *Neuron*, 13:813–821 (1994); and Tajbakhsh et al., *Nature* 384:266–270 (1996)), but with the following differences: (1) The fusion protein contains the complete myf5 coding sequence fused to the ha β-gal. (2) The fusion protein coding sequence is followed by a neomycin resistance gene flanked by FRT sites (FLP recombinase targets). This allows G418 selection of ES cells that have taken up and integrated the targeting construct. (3) A diphtheria toxin expression cassette is located 5' of the region of homology with the myf5 mouse genomic DNA. During homologous recombination, strand exchange will occur within the homology region and as a result the diphtheria toxin expression cassette will be excluded following integration (Capecchi, *Science*, 244: 1288–1292 (1989)). Clones resulting from random integration rather than homologous recombination retain diphtheria toxin expression and will be selected against during culture, because they will die. The surviving clones are characterized by PCR, and the appropriate integration of the construct in the myfS genomic locus is confined by Southern blot.

Subsequently, the neomycin selection cassette is removed using a modified version of a previously described technique (Fiering et al., *Genes Dev.*, 9:2203–2213 (1995)). Briefly, a plasmid expressing a bicistronic message containing FLP recombinase, an Internal Ribosomal Entry Site (IRES) and GFP is transiently transfected into the ES cell clones. GFP positive cells are clonally sorted using the fluorescence activated cell sorter (FACS). In these cells, FLP deletes the sequences between the two FRT sites, and only the β-gal coding sequence remains in the ES cell genome. Aliquots of the sorted clones are tested for sensitivity to G418, and in the sensitive clones the accurate deletion of the neomycin cassette is confirmed by PCR and Southern blotting. This approach, which eliminates the selectable marker, avoids interference between the exogenous promoter driving the selectable marker and the endogenous regulatory sequences as described (Olson et al., *Cell*, 85:1–4 (1996)).

Targeting constructs for MyoD and Mtwist have also been described (Rudnicki et al., *Cell*, 71:383–390 (1992); Chen and Behringer, *Genes Devel.*, 9:686–699 (1995)) and the relevant constructs may be produced for each. Based on these available reagents, and following the scheme proposed above for the myf5-Δα strategy, vectors to target (Chen and Behringer, *Genes Devel.*, 9:686–699 (1995)) MyoD-Δα and Mtwist-Δω fusions into the endogenous MyoD and Mtwist loci of ES cells may be constructed. In each case, an ES cell line syngeneic to the available genomic DNA homology regions in the targeting construct are used, as strain differences are known to reduce the frequency of homologous recombination. The same FLP-mediated excision methodology used for the myf5 "knock in" described above is applied to the deletion of the neomycin resistance markers from the targeted MyoD and Mtwist loci. This "in-out" strategy ensures that the fusion protein coding regions are under the control of the endogenous regulatory elements and associated with minimal extraneous flanking DNA sequences.

Example 9
Analysis of the myf5-Δα/Mtwist-Δω and MvoD-Δα/Mtwist-Δω Transgenic Lines For each construct, multiple ES cell clones are injected into blastocysts. The chimeric offspring obtained upon implantation into pseudopregnant females are tested for germline transmission, and heterozygous mice are obtained. One critical control in this experiment is to confirm that the expression pattern of the "knocked-in" fusion proteins faithfully mimics that reported for the corresponding endogenous factors. For this purpose, a system allowing rapid detection of the fusion proteins is provided. A transgenic mouse strain expressing a β-gal mutant (Δμ) capable of strong complementation with either Aa or Aco is generated. Δμ is expressed ubiquitously from the strong chicken β-actin promoter. MyoD-Δα, myf5-Δα and Mtwist-Δω transgenic mouse lines are each crossed with the Δμ transgenic mice. Since co-expression of any of these fusion proteins with the strongly complementing Δμ mutant should result in readily detectable β-gal activity, it is thus possible to follow the expression pattern of our fusion proteins by X-gal staining of the embryos.

The Mtwist-Δω mouse line is crossed with MyoD-Δα and myf5-Δα transgenic mouse lines. As heterozygous mice are used for these crosses, on average ¼ of the embryos will be double heterozygotes. These embryos are analyzed at different time points during development by staining whole mount preparations and histological sections with X-gal. The sections also are stained with the more sensitive Fluor-X-Gal fluorescent substrate (Mohler, W. A., & Blau, H. M., *Proc. Natl. Acad. Sci.*, USA, 93:12423–12427 (1996)), to detect those cells in which the Mtwist-MyoD or the Mtwist-myf5 interaction is a rare event and the β-gal signal is consequently lower.

The strength of this approach is that β-gal activity should only appear in cells in which the interactions described above take place in vivo. This approach allows a thorough analysis of the interplay between inhibitors and activators of myogenesis during development. In particular, it allows analysis of the correlation between co-expression and a physical interaction of two proteins as heterodimers in an in vivo setting, the developing mouse embryo. This is particularly important in the case of factors which, like Mtwist, are known to be involved in multiple control steps (Chen and Behringer, *Genes Devel.*, 9:686–699 (1995)) and are likely to carry out their functions through interaction with different determination factors.

The use of β-gal complementation mutants also can be extended to an analysis of I-mf. I-mf has also been implicated as a negative regulator of myogenesis in the embryo (Chen et al., *Cell*, 86:731–741 (1996)). Interestingly however, I-mf and Mtwist are co-expressed throughout most of the somite. It is not clear if their presence in the same cells is merely an indication of the existence of redundant mechanisms for repressing the activity of the myogenic HLH regulators or whether the two factors have distinct functions. In the first case, the prediction would be that both I-mf and Mtwist associate with the same factors. In the second case, differences and interactions with different factors should be detectable using our experimental approach.

Example 10
Analysis of Protein Interactions by Fluorescence-Activated Cell Sorting (FACS)

The β-gal activity of a population of C2C12 cells that were coinfected with FRAP-Δα and FKBP12-Δω (as described in Examples 1 and 2) was assayed in the presence and absence of 10 ng/ml rapamycin by FACS. FACS was carried out according to methods that are well-known in the art, e.g., Nolan et al. (1988) *Proc. Natl. Acad. Sci. USA* 85:2603–2607. Using this assay, increased β-gal activity was detected in the majority of cells after 90 minutes of rapamycin treatment (FIG. 6A). A range of expression levels was observed, as evidenced by the breadth of the peak of emission in the presence and absence of the drug (compare light and dark profiles in FIG. 6A). This breadth is presumably due to variable efficiency of expression of each of the retroviral vectors following integration in the target cell. This inference is supported by the finding that when the 25% of cells expressing the lowest β-gal activity in the absence of rapamycin were collected (FIG. 6B) and reassayed in the presence and absence of rapamycin, the treated and untreated cell populations yield non-overlapping peaks by FACS analysis, indicating a clear distinction between the treated (light peak) and untreated (dark peak) populations (FIG. 6C). Thus, non-overlapping populations of cells distinguished by the expression (or non-expression) of complementing fusion proteins can be identified and isolated by FACS.

Example 11
Monitoring of EGF Receptor Dimerization in Living Cells

A previously unrecognized mode of regulation of the epidermal growth factor (EGF) receptor signaling pathway that acts through receptor dimerization was revealed using the methods of the invention for monitoring protein-protein interactions at the membrane of live cells. Chimeric proteins containing the extracellular and transmembrane domains of the EGF receptor, fused to weakly complementing β-galactosidase (β-gal) deletion mutants, were expressed in myoblasts. Treatment of the cells with EGF resulted in chimeric receptor dimerization as assessed by a rapid increase in β-gal enzymatic activity. Further treatment with EGF did not restimulate dimerization unless an inhibitor of EGF receptor tyrosine kinase was added. These results reveal a feedback mechanism in which tyrosine kinase activity of the dimeric receptor inhibits further dimerization of the receptor.

METHODS
Construction of Chimeric Receptors

The weakly complementing Δα and Δω deletion mutants of β-gal were each linked to a polypeptide sequence containing the extracellular and transmembrane domains of the human EGF receptor to form chimeric receptor molecules. The chimeric receptors lacked the cytoplasmic domain, and attendant tyrosine kinase activity, of the native receptor. The procedure was as follows. The sequence coding for the extracellular and transmembrane domains of the human EGF receptor (amino acids 1–655) was amplified by polymerase chain reaction (PCR) using primers that incorporated an NcoI site at the 5' end and an XhoI site at the 3' end of the PCR product. Although this fragment retains threonine 654, which is a site of protein kinase C (PKC) phosphorylation, arginines 656 and 657 are removed, destroying the consensus PKC recognition sequence. The amino acid sequence beginning with threonine 654 is thr-leu-glu-ser-met, with the met residue being the beginning of the β-gal sequence. The glu and ser codons are generated by the junction sequence and are not native to either EGF or β-gal.

DNAs encoding the chimeric receptors were inserted into a retroviral vector also encoding a selectable marker. For the construct containing the EGOF receptor-Δα fusion, the selectable marker was the neo gene, encoding G418 resistance; while the EGF receptor-Δω fusion specified hygromycin resistance (FIG. 1B). Accordingly, the EGF receptor PCR product was digested and cloned into the NcoI and XhoI sites of the pWZL-Δα and pWZL-Δω vectors. The pWZL-Δα-neo and pWZL-Δω-hygro plasmids were constructed by cloning the lacZ Δα and Δω deletion mutants into pWZL-neo and pWZL-hygro, respectively. Mohler et al., supra; and Rossi et al. (1997) *Proc. Natl. Acad. Sci. USA* 94:8405–8410. Plasmids were transfected into φNX cells using Lipofectamine (Life Technologies), and virus-containing supernatant was harvested 48–72 hours later. C2F3 mouse myoblasts (Rastinejad et al. (1993) *Cell* 72:903–917) maintained in DME with 20% fetal bovine serum (FBS) in 10% $CO_2$, were infected by overnight incubation in the viral supernatant. Cells containing both constructs were selected in 1mg/ml G418 plus 1 mg/ml hygromycin, and were maintained in 400 μg/ml of each antibiotic.

EGF Treatment and FACS Analysis

Cells were treated with mouse salivary gland EGF (Sigma) at 100 ng/ml and in some experiments were treated with tyrphostin AG1478 (Calbiochem) at 100 nM. Following all treatments, cells were rinsed with phosphate buffered saline (PBS), trypsinized, and resuspended in PBS+5% FBS. Fluorescein di-β-D-galactopyranoside (FDG; Molecular Probes) was loaded into the cells by hypotonic shock as described. Fiering et al. (1991) *Cytometry* 12:291–301 and Nolan et al (1988) *Proc. Natl. Acad. Sci. USA* 85:2603–2607. Cells were kept on ice until analysis on the cell sorter, which was conducted 1 to 2 hours after trypsinization.

The chimeric receptor was detected by immunofluorescence using a monoclonal mouse anti-human EGF receptor antibody diluted 1:100 (clone EGFR1, Dako) and either phycoerythrin-labeled horse anti-mouse IgG (Vector) or fluorescein-labeled goat anti-mouse IgG (Cappel) diluted 1:100. Cells were trypsinized and stained in PBS+5% FBS. For each sample, FACS analysis data was collected for 5000 cells. Cells were cloned on a Becton-Dickinson FACS Vantage and analyzed on a Becton-Dickinson FACScan at the Stanford Shared FACS Facility. Data analysis was facilitated by FlowJo software (Tree Star, Inc.). Data shown here as FACS profiles were adjusted for autofluorescence using autofluorescence compensation. Alberti et al. (1987) *Cytometry* 8:114–119. Mean fluorescence data were adjusted for autofluorescence and for endogenous mammalian β-gal activity by subtracting the mean fluorescence of untransduced cells loaded with FDG substrate.

RESULTS
Receptor Dimerization Assay

Figure 7B:
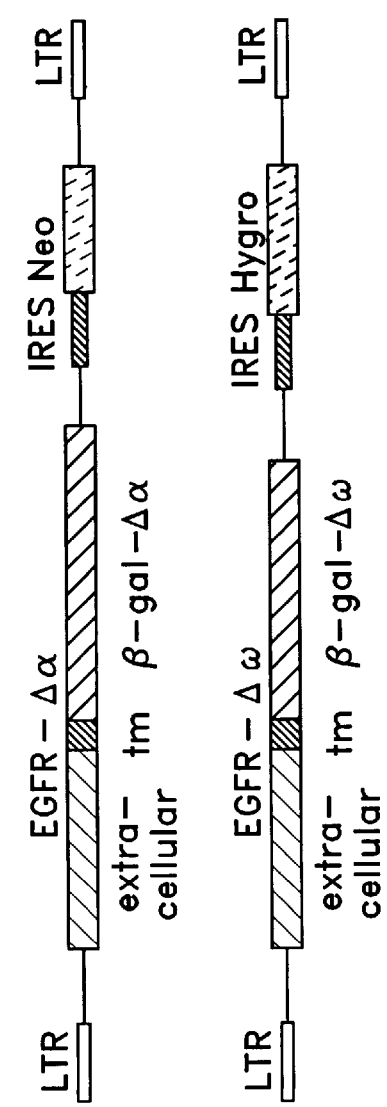
Figure 7D:
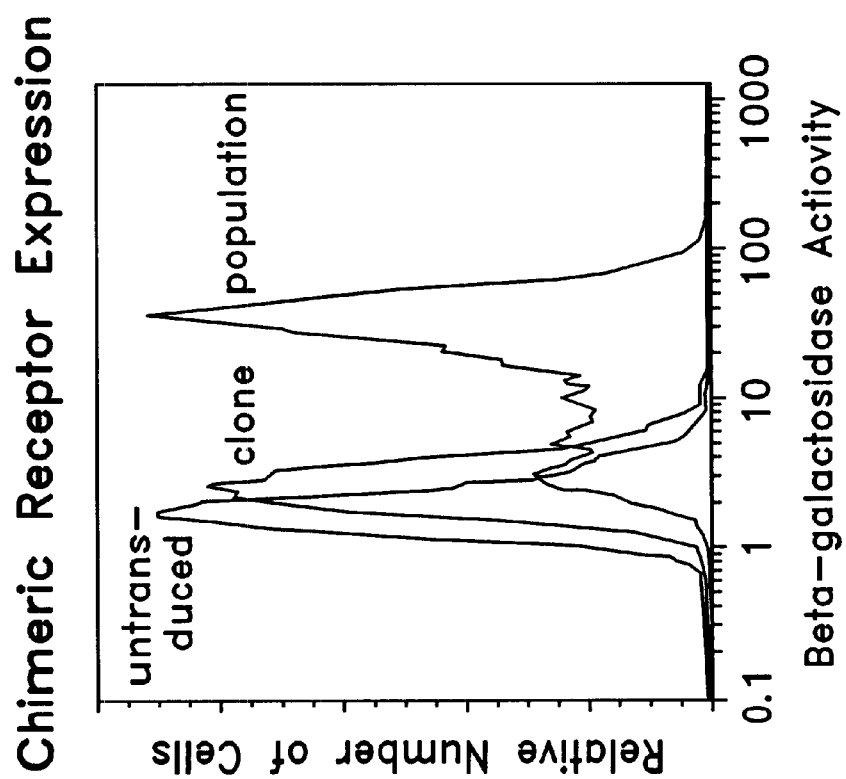
Figure 7C:
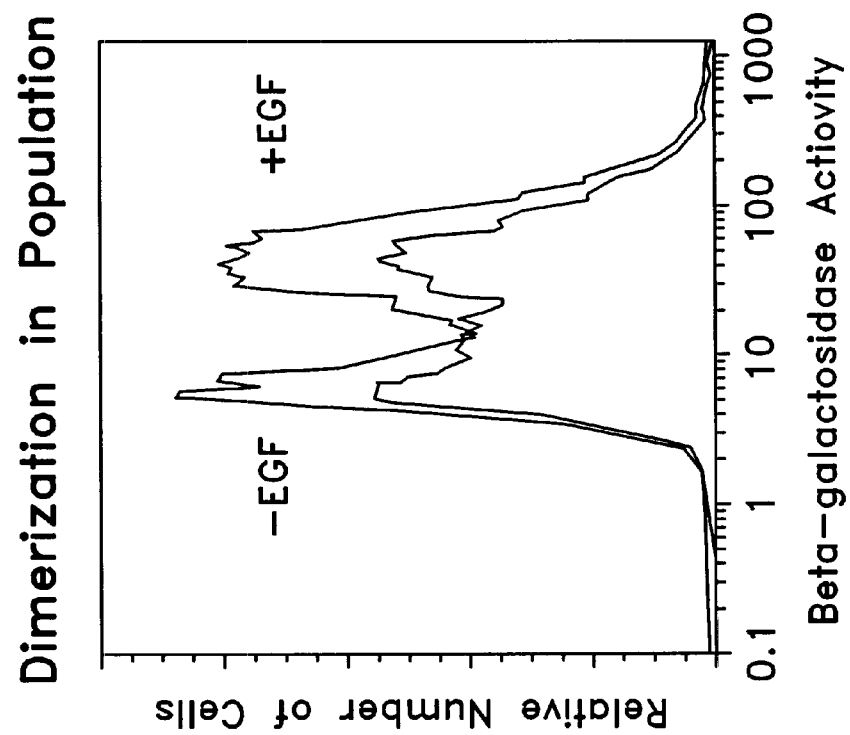
Figures 7E, 7F:
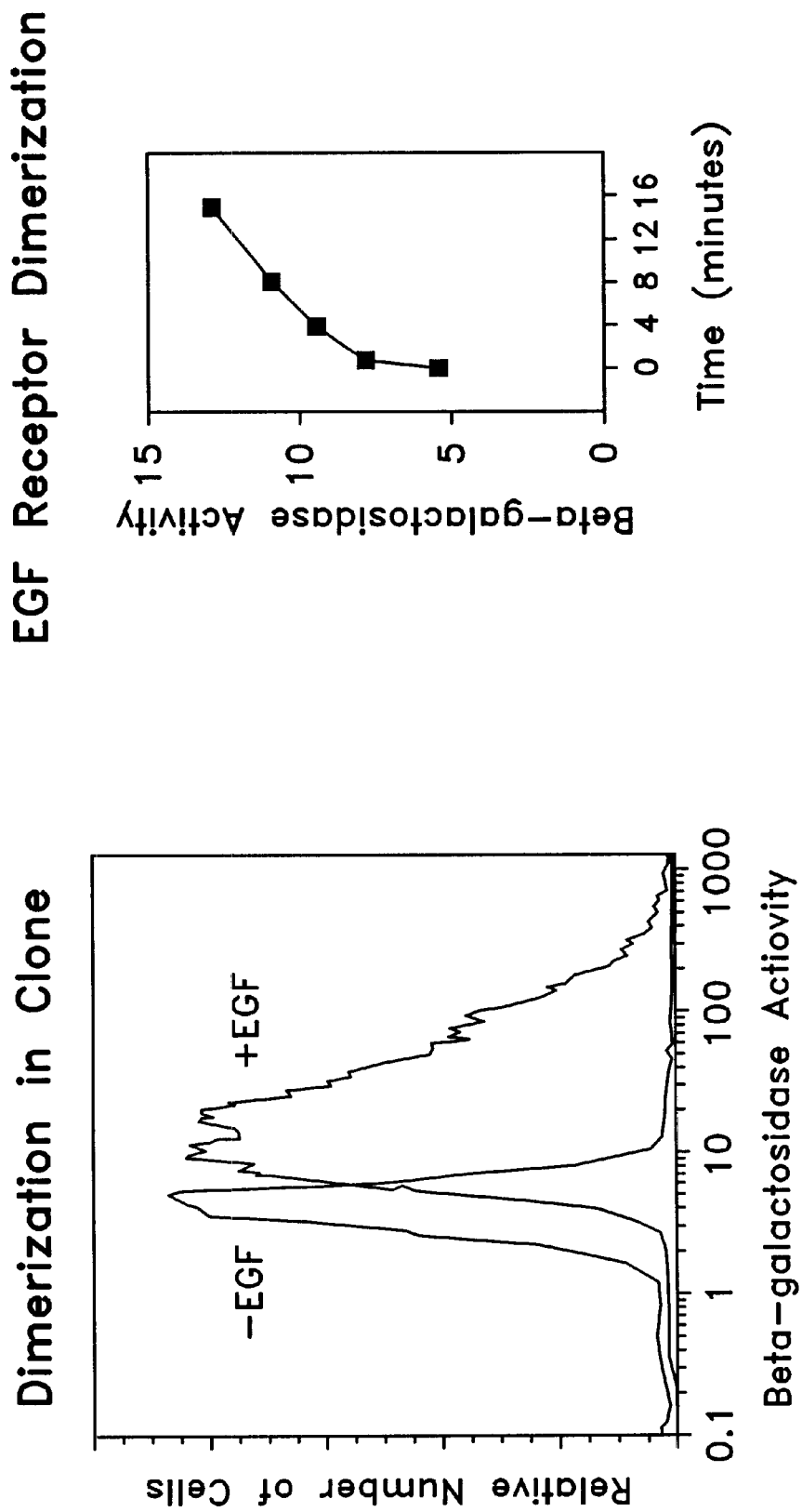

The two chimeric DNAs were each cloned into retroviral vectors encoding selectable markers (FIG. 7B) and transduced into the C2F3 mouse myoblast cell line. After selection with G418 and hygromycin, β-gal enzyme activity was monitored using the fluorescence activated cell sorter (FACS) to measure the cleavage product of a fluorogenic substrate. In the absence of EGF, the population of transduced cells consisted of a mixture of cells with low and high levels of β-gal activity (FIG. 7C, light gray curve), which was not unexpected given that the EGF receptor is capable of dimerizing in the absence of EGF. Gadella et al. (1995) *J. Cell Biol.* 129:1543–1558. Following stimulation of the population of cells with EGF many of the cells exhibited increased β-gal activity (FIG. 7C, dark gray curve). FACS analysis with an antibody specific to the human EGF receptor showed that the cells expressed a broad range of levels of the chimeric receptor (FIG. 7D, medium gray curve). Clones from this population were isolated and screened for low background levels of β-gal activity in the absence of EGF, and increased levels of β-gal activity in the presence of EGF. One such clone had a low level of chimeric receptor expression relative to the population (FIG. 7D, dark gray curve) and exhibited a several-fold increase in β-gal activity in the presence of EGF (FIG. 7E), indicating dimerization of the chimeric receptor. Dimerization was also observed following stimulation with other EGF-like growth factors that bind and activate the EGF receptor, such as TGF-α, heparin-binding EGF-like growth factor, and betacellulin; but not with EGF-like factors, such as heregulin α, that act through related receptors other than the EGF receptor. Beerli et al. (1996) *J. Biol. Chem.* 271:6071–6076. Dimerization, expressed as the mean fluorescence or β-gal activity of the cells, could be detected with EGF treatments as short as one minute, and dimerization increased rapidly with longer exposure to EGF (FIG. 7F).

Time-course of EGF Receptor Dimerization

Figure 8:
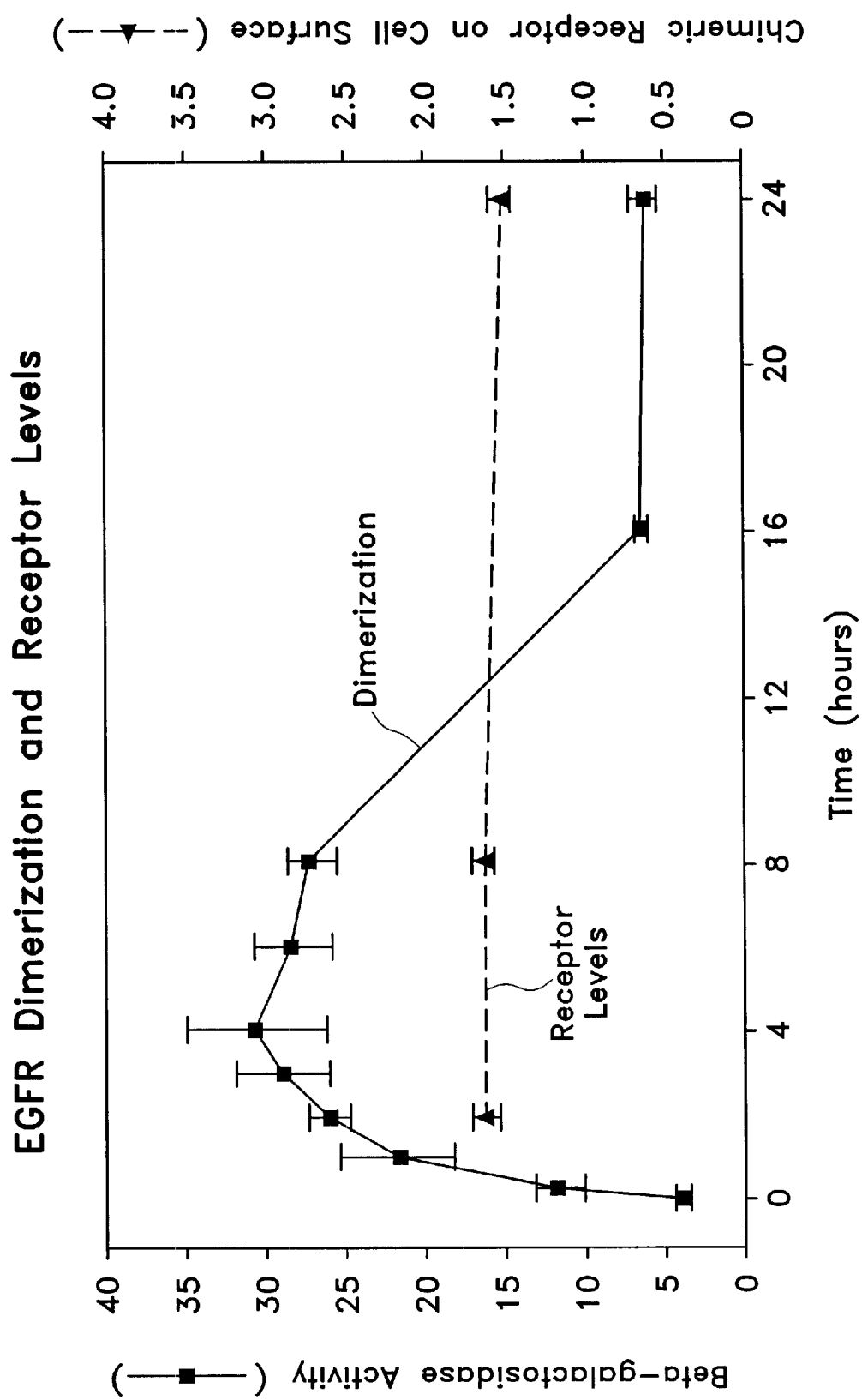
FIG. 8 shows a time-course of EGF receptor dimerization and receptor expression on the cell surface, following treatment with EGF. Cells expressing chimeric receptors were treated with 100 ng/ml EGF for 0 to 24 hours. Dimerization, as measured by β-gal activity, was monitored by FACS, and the mean β-gal activity (fluorescein fluorescence) of the cells was plotted (left-hand axis; -■-). Chimeric receptor levels on the cell surface were measured on the FACS using a monoclonal antibody to the extracellular domain of the human EGF receptor and a phycoerythrin-labeled second antibody. Mean phycoerythrin fluorescence values are shown on the right-hand axis (--▲--). Triplicate samples were analyzed for each time point, and 5000 cells were analyzed for each sample. The error bars indicate the standard deviation of the replicate samples.

In order to follow the fate of receptor dimers over time, cells from the same clone described above were cultured in media containing EGF for 0 to 24 hours and then analyzed by FACS. Dimerization peaked after 2 to 4 hours in EGF, and then decreased (FIG. 8). The fold increase in dimerization and the rate of the ensuing decline in dimerization differed among experiments, but the overall pattern was consistent, and was also observed with the original population of uncloned cells. By contrast, measurement of the levels of the chimeric receptor on the cell surface by immunofluorescence using the FACS showed that the amount of chimeric receptor on the cell surface remained essentially constant over the period that dimerization markedly decreased (FIG. 8, dashed line). It was concluded that the decline in dimerization was due to either the depletion of EGF from the media, or to an inhibition of receptor dimerization.

Feedback Regulation of EGF Receptor Dimerization

During the decline in dimerization, the response to a second EGF treatment was minimal, suggesting that the cells were resistant to further EGF-mediated dimerization despite the continued presence of the chimeric receptor on the cell surface. By contrast, if, following EGF treatment, cells were incubated in media lacking EGF for several hours, dimerization could be restimulated with a second treatment of EGF. This indicated that the continued presence of EGF in the media was the basis for the continued inhibition of dimerization of the receptor. A possible explanation for these results is that signaling through the endogenous wild-type EGF receptors in the cells inhibits dimerization of the chimeric receptor. A test of this hypothesis was possible, using AG1478, a highly specific inhibitor of the EGF receptor tyrosine kinase. Levitzki et al. (1995) *Science* 267:1782–1788.

Figure 9A:
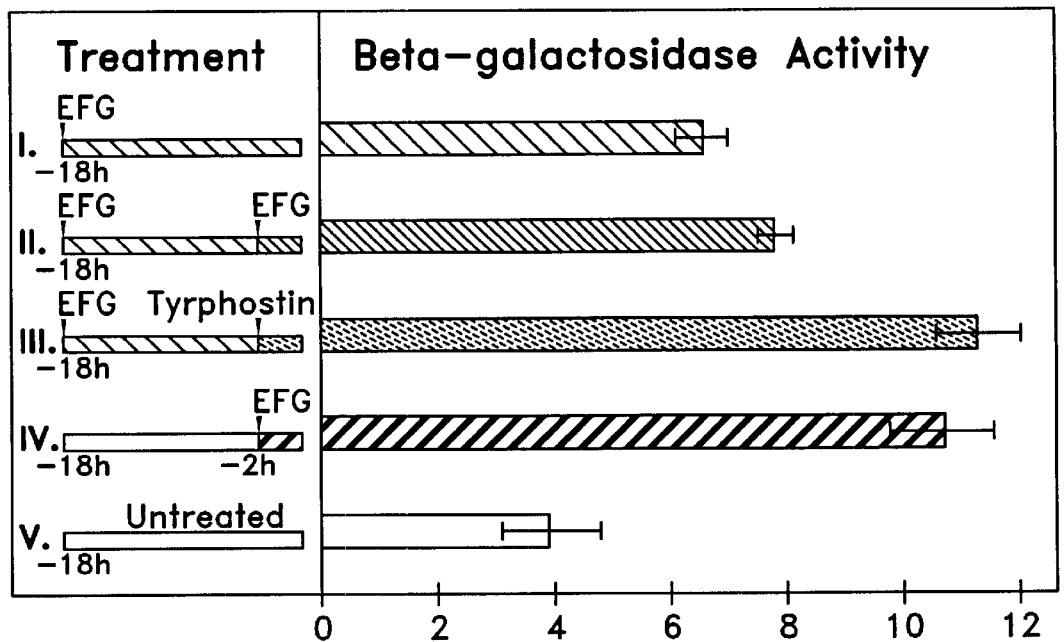
FIGS. 9A–9B show that EGF receptor dimerization is enhanced by tyrphostin AG1478.
Figure 9B:
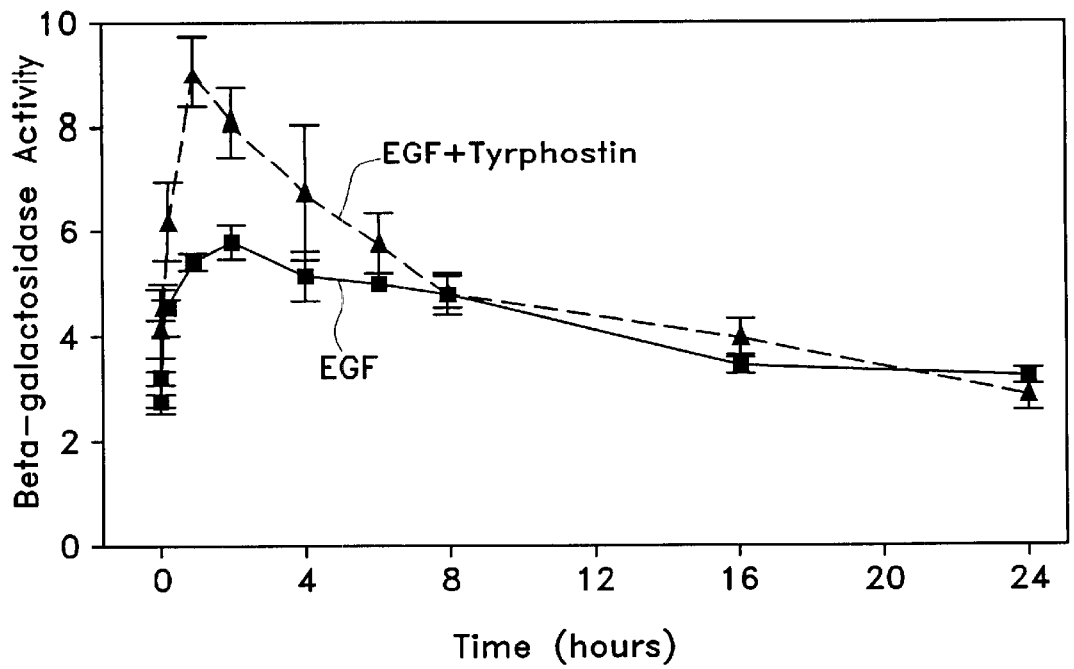

Accordingly, cells expressing chimeric receptor were treated with EGF overnight, and then retreated with EGF or tyrphostin. As shown in FIG. 9A (left panel), sample I received a single overnight treatment with 100 ng/ml EGF. Samples II and III also were treated with EGF overnight, and then retreated with 100 ng/ml EGF for 2 hours (sample II), or 1.00 nM tyrphostin AG1478 for 2 hours (sample III). Sample IV received a single 2 hour treatment with 100 ng/ml EGF, and sample V received no treatment. The results (FIG. 9A, right panel) show that treatment of the cells with tyrphostin led to an increase in dimerization, yielding dimerization levels that were comparable to the peak levels observed after a single two hour treatment with EGF, indicating that EGF receptor tyrosine kinase activity is involved in inhibiting receptor dimerization. Tyrphostin treatment also caused an increase in the amount of β-gal activity observed when previously unstimulated cells were treated with EGF. Cells were treated with EGF and tyrphostin, or EGF alone, over periods ranging from 0–24 hours. Cells that received both tyrphostin and EGF showed greater β-gal activity than cells that received EGF alone, for treatment times of up to 6 hours (FIG. 9B). By 8 hours of treatment, there was no difference in EGF receptor dimerization between EGF-treated cells and EGF+tyrphostin-treated cells. Repeated administration of tyrphostin every four hours did not further prolong the increased β-gal activity.

These results show that inhibition of receptor tyrosine kinase can relieve a feedback inhibition of receptor dimerization. Protein kinase C phosphorylation can decrease receptor binding affinity for EGF by phosphorylating the receptor on sites in the cytoplasmic domain. However, since the chimeric receptor used in the experiments described herein lacks the known sites of PKC phosphorylation, the inhibition of dimerization observed with this receptor must be mediated through the extracellular or transmembrane regions of the receptor.

These results also demonstrate that, using the methods and compositions of the invention, it is possible to monitor EGF receptor dimerization in live cells. They show, in addition, that receptor kinase activity is involved in regulating dimerization, the first step after ligand binding in EGF signal transduction. Dimerization is measurable following treatment of cells with EGF after as little as one minute, which indicates that the β-gal complementation is able to monitor the rapid production of newly formed protein dimers. Previous data on EGF binding, receptor internalization, and substrate phosphorylation also indicate that the receptor responds to ligand within minutes. Felder et al. (1992) *J. Cell. Biol.* 117:203–212; and Kiyokawa et al. (1997) *J. Biol. Chem.* 272:18656–18665. Although receptor dimerization declines after a few hours, the chimeric receptor remains on the cell surface and is refractory to further dimerization in response to EGF. Inhibition of the endogenous receptor tyrosine kinase, however, permits further dimerization. Inhibition of receptor dimerization begins immediately following receptor activation, as shown by the observation that including tyrphostin with the initial EGF treatment increases dimerization over the levels observed with EGF alone.

The kinetics of Complementation Reflect the Kinetics of Association of the Binding Partners The decline in EGF receptor dimerization is in contrast to observations using β-gal complementation to monitor the interaction of FRAP and FKBP12. See Examples 1, 2 and 10, supra; see also Rossi et al. (1997), supra. Using β-gal complementation to detect the rapamnycin-mediated interaction between FRAP and FKBP12, the slowest increase in β-gal activity was seen at the earliest time points following the addition of rapamycin, but β-gal activity continued to increase for at least 20 hours. This could be due to stabilization of the chimeric protein interactions by formation of the active β-gal complex. With EGF receptor dimerization, however, the most rapid increase in β-gal activity was seen at the earliest time points after the addition of EGF to the media; whereas, after 2 to 4 hours, the β-gal activity declined. The difference between these results indicates that the dimerization kinetics observed with β-gal complementation are not simply a reflection of β-gal complementation kinetics or stabilization, but reflect, at least to some degree, the kinetics of interaction of the non-β-gal portions of the chimeric proteins. The results also show that β-gal complementation can monitor the regulation of dimerization by other proteins.

Comparison to Previous Methods

Receptor dimerization has typically been studied by in vitro methods such as chemical cross-linking and immunopurification, followed by gel electrophoresis. Yarden et al. (1987) Biochemistry 26:1443–1451. Recently, EGF receptor dimerization has also been analyzed by fluorescence resonance energy transfer (FRET). Gadella et al. (1995) supra. Fluorescein and rhodamine labeled EGF was added to cells, and dimerization of the receptor was measured microscopically. Low temperature incubations and fixation of the cells was required to prevent internalization of the receptor before analysis, a problem that was avoided in the present experiments by using a non-internalizing mutant receptor. FRET can also be used to study interactions of fluorescently-labeled molecules within the cell or cell membrane; however, labeling and introduction of these molecules at sufficiently high concentration can be cumbersome. It has recently been shown that green fluorescent protein can be modified and used for FRET analysis on genetically expressed proteins. Miyawaki et al. (1997) Nature 388:882–887. The GFP signal, however, cannot be enzymatically amplified as is the case with β-gal.

Thus, β-gal complementation provides a rapid method for monitoring receptor dimerization in live cells. This method can be used for high throughput screening for pharmacological agents that can bind to a number of receptors and act as either agonists or antagonists. Binding data alone cannot indicate whether or not an agent can elicit a response; identifying a response, by analysis of downstream effects such as phosphorylation, involves destruction of the cells followed by in vitro analysis. β-gal complementation will also enable a screen for novel dimerization partners in a mammalian "two-hybrid" assay that, in the case of membrane receptors, can offer new insight into the regulation of signal transduction pathways.

Although the foregoing invention has been described in some detail by way of illustration and example for purposes of clarity of understanding, it will be apparent to those skilled in the art that certain changes and modifications may be practiced. Therefore the foregoing descriptions and examples should not be construed as limiting the scope of the invention.

What is claimed is:

1. A reporter system component comprising:
   a first low-affinity reporter subnit, coupled to a first putative binding moiety;
   wherein the first low-affinity reporter subunit associates with at least a second low-affinity reporter subunit to generate an enzymatically active complex, said association being mediated by the first putative binding moiety.

2. The reporter system component of claim 1 wherein the first putative binding moiety is a protein.

3. The reporter system component of claim 2 wherein the protein is selected from the group consisting of members of a signal transduction cascade, cell surface receptors, proteins regulating apoptosis, proteins that regulate progression of the cell-cycle, proteins involved in the development of tumors, transcriptional-regulatory proteins, translational regulatory proteins, proteins that affect cell interactions, cell adhesion molecules, proteins which are members of ligand-receptor pairs, proteins that participate in the folding of other proteins, and proteins involved in targeting to intracellular compartments.

4. A reporter system comprising the reporter system component of claim 1 and further comprising at least a second low-affinity reporter subunit coupled to a second putative binding partner of the first putative binding moiety.

5. The reporter system of claim 4 wherein the binding affinity of the putative binding moieties for each other is greater than the binding affinity of the first and second reporter subunits for each other.

6. The reporter system of claim 5 wherein the generation of the enzymatically active complex is dependant upon the binding of the putative binding moieties.

7. The reporter system of claim 4 wherein the first putative binding moiety and the second putative partner comprise identical molecules.

8. The reporter system of claim 4 wherein the first and second putative binding moieties are proteins.

9. The reporter system of claim 7 wherein the protein is selected from the group consisting of members of a signal transduction cascade, cell surface receptors, proteins regulating apoptosis, proteins that regulate progression of the cell-cycle, proteins involved in the development of tumors, transcriptional-regulatory proteins, translational regulatory proteins, proteins that affect cell interactions, cell adhesion molecules, proteins which are members of ligand-receptor pairs, proteins that participate in the folding of other proteins, and proteins involved in targeting to intracellular compartments.

10. The reporter system of claim 7, wherein the first and second reporter subunits each comprise a protein, and wherein said proteins are capable of associating to catalyze a reaction to produce a detectable signal.

11. The reporter system of claim 10 wherein the associated reporter subunits catalyze a reaction to produce a product which is directly detectable as the detectable signal.

12. The reporter system of claim 7 wherein the first and second subunits are low affinity binding mutant subunits of a hydrolytic enzyme.

13. The reporter system of claim 12 wherein the first and second subunits are low affinity binding mutant subunits of β-galactosidase.

14. The reporter system of claim 10, wherein the detectable signal is amplifiable.

15. The reporter system of claim 8 wherein the first and second subunits are low affinity binding mutant subunits of an enzyme.

16. The reporter system component of claim 1 wherein said component comprises a fusion protein including said low affinity reporter subunit and said first putative binding moiety.

17. The reporter system component of claim 16 wherein the low affinity reporter subunit of β-galactosidase.

18. A nucleic acid encoding the fusion protein of claim 16.

19. The nucleic acid of claim 18 further comprising regulatory sequences effecting expression of the putative binding protein.

20. The reporter system component of claim 17 wherein the fusion protein further comprises an additional protein sequence between said reporter subunit and said putative binding moiety.

21. A viral vector comprising the nucleic acid of claim 18.

22. A cell transformed with the nucleic acid of claim 18.

23. A cell transformed with a nucleic acid encoding the reporter system component of claim 13 and a nucleic acid encoding at least a second of said reporter system components.

24. The reporter system of claim 1, wherein the low-affinity reporter subunits comprise an enzyme and an inhibitor of the enzyme.

25. A method of determining the occurrence of binding between first and second putative binding moieties, the method comprising:
   a) providing a reporter system comprising:
      a first component comprising a first low affinity reporter subunit, coupled to the first putative binding moiety, and
      a second component comprising a second low affinity reporter subunit coupled to the second putative binding moiety;
         wherein the first low affinity reporter subunit associates with at least the second low affinity reporter subunit to generate an enzymatically active complex, said association being mediated by the binding of the first and second putative binding moieties;
   b) combining the first component and the second component; and
   c) detecting the presence or absence of enzyme activity.

26. The method of claim 25 wherein the binding affinity of the putative binding moieties for each other is greater than the binding affinity of the first and second reporter subunits for each other.

27. The method of claim 25 wherein the first and second putative binding moieties are proteins.

28. The method of claim 27 wherein the protein is selected from the group consisting of members of a signal transduction cascade, cell surface receptors, proteins regulating apoptosis, proteins that regulate progression of the cell-cycle, proteins involved in the development of tumors, transcriptional-regulatory proteins, translational regulatory proteins, proteins that affect cell interactions, cell adhesion molecules, proteins which are members of ligand-receptor pairs, proteins that participate in the folding of other proteins, and proteins involved in targeting to intracellular compartments.

29. The method of claim 25, wherein the first and second reporter subunits each comprise a protein, and wherein said proteins are capable of associating to catalyze a reaction to produce a detectable signal.

30. The method of claim 29 wherein the associated reporter subunits catalyze a reaction to produce a product which is directly detectable as the detectable signal.

31. The method of claim 30 wherein the first and second subunits are low affinity binding mutant subunits of β-galactosidase.

32. The method of claim 25 wherein each of said first and second components comprises a fusion protein.

33. The method of claim 32 wherein the low affinity reporter subunit comprises a low affinity binding mutant subunit of β-galactosidase.

34. The method of claim 32 wherein step (a) comprises transforming a cell with one or more nucleic acids encoding the fusion proteins.

35. The method of claim 34 wherein step (c) comprises detecting the presence or absence of enzymatic activity within the cell.

36. The method of claim 35, wherein the intracellular localization of the enzymatic activity is determined.

37. The method of claim 34 wherein the one or more nucleic acids encoding the fusion proteins further comprise sequences regulating expression of the putative binding protein.

38. The method of claim 34 wherein the fusion proteins are encoded by a viral vector.

39. The method of claim 32 wherein the fusion protein further comprises a protein sequence between said reporter subunit and said putative binding moiety.

40. The method of claim 25 wherein the degree of binding is quantitated.

41. The method of claim 25 wherein the method further comprises detecting the effect of a third moiety on the binding of the first and second binding moieties, the method further comprising, after step (a) and prior to step (b), combining said reporter system with said third moiety.

42. The method of claim 25 wherein step (b) comprises combining the first and second components in the presence of a substance to determine the effect of the substance on binding of the first and second binding moieties.

43. The method of claim 42 wherein the substance is a putative binding inhibitor of binding moieties having a predetermined binding affinity, and wherein the absence of enzymatic activity in step (c) provides an indicator that the substance is a binding inhibitor.

44. The method of claim 42 wherein the substance is a putative promoter of binding between binding moieties having low or substantially no binding affinity for each other, and wherein the presence of enzymatic activity in step (c) provides an indicator that the substance is a promoter of binding of the binding moieties.

45. The method of claim 42 wherein the first and second reporter units, and first and second binding moieties, each are proteins;
   wherein the components provided in step (a) each comprise a fusion protein including the reporter subunit and the binding moiety;
   wherein step (b) comprises expressing nucleic acid sequences encoding the first and second components within a cell suspected to contain the substance which inhibits or promotes binding of the binding moieties; and
   wherein step (c) comprises detecting the presence or absence of enzymatic activity in the cell or lysate thereof, thereby to determine the presence or absence in the cell of the substance which acts as an inhibitor or promoter of binding between the binding moieties.

46. The method of claim 42 wherein the substance is selected from the group consisting of a protein, lipid, carbohydrate, nucleic acid, and a small molecule pharmaceutical.

47. The method of claim 42 wherein the substance is a peptide, drug or synthetic analog.

48. The method of claim 42, wherein the substance directly of indirectly affects an upstream event which results in an effect on binding of the first and second binding moieties.

49. A method of screening for binding of a first binding moiety with members of a plurality of different second putative binding moieties, the method comprising:
   a) providing a plurality of reporter systems each comprising:
      a first component comprising a first low affinity reporter subunit coupled to the first binding moiety, and
      one of a plurality of second components each comprising a second low affinity reporter subunit coupled to one of said plurality of second putative binding moieties, wherein in each of said second components, said second putative binding moiety is different;
         wherein the first low affinity reporter subunit associates with the second low affinity reporter subunit to generate an enzymatically active complex upon the binding of the first binding moiety with one of said different second putative binding moieties;
   b) individually combining the first component with each of the plurality of second components to produce a plurality of binding assay samples, each of which includes the first component and a different one of the second components; and
   c) detecting the presence or absence of enzymatic activity in each of the binding assay samples.

50. The method of claim 49 wherein the first and second components each comprise a fusion protein including the binding moiety and the reporter subunit.

51. The method of claim 50 wherein, in step (b), the components are expressed from a nucleic acid sequence introduced into a cell.

52. The method of claim 51, wherein the plurality of second putative binding moieties are encoded by members of a cDNA library.

53. The method of claim 52, wherein the cell is a eukaryotic cell.

54. The method of claims 53, wherein the cell is a mammalian cell.

55. The method of claim 54, wherein the cell is a human cell.

56. The method of claim 49, wherein, in step (c), enzymatic activity is quantitated.

57. The method of claim 49, wherein cells in which binding between the first binding moiety and one of the plurality of putative second binding moieties has occurred are separated from cells in which said binding has not occurred.

58. The method of claim 57, wherein separation is by fluorescence-activated cell sorting.

59. The method of claim 49, wherein the first binding moiety is selected from the group consisting of cell surface receptors, transcriptional regulatory proteins, translational regulatory proteins, replication proteins, splicing proteins, signal transduction proteins, cell-cell adhesion molecules, cell-substrate adhesion molecules, cell-cycle proteins, oncogene products, tumor suppressor proteins, membrane receptors, proteins regulating apoptosis, developmental regulatory proteins, proteins that affect cell interactions, proteins that participate in the folding of other proteins, proteins involved in targeting to intracellular compartments, viral proteins, and cytoskeletal proteins.

60. The method of claim 49, wherein the first and second reporter subunits are low affinity binding mutant subunits of β-galactosidase.

61. A method of determining the occurrence of association between first and second moieties, the method comprising:
   a) providing a reporter system comprising:
      a first component comprising a first low affinity reporter subunit, coupled to the first moiety, and
      a second component comprising a second low affinity reporter subunit coupled to the second moiety;
         wherein the first low affinity reporter subunit associates with at least the second low affinity reporter subunit to generate an enzymatically active complex, said association being mediated by association between the first and second moieties, wherein association between the first and second moieties is mediated by a third moiety;
   b) combining the first component, the second component and the third moiety; and
   c) detecting the presence or absence of enzyme activity.

62. The method of claim 61 wherein the association between the first and second moieties is mediated by multiple additional moieties.

63. The method of claim 61, wherein the first and second reporter subunits are low affinity binding mutant subunits of β-galactosidase.

64. A reporter system component comprising:
   a first low-affinity reporter subunit, coupled to a first putative binding moiety; wherein the first low-affinity reporter subunit associates with at least a second low-affinity reporter subunit to generate a detectable signal in situ in a cell, said association being mediated by the first putative binding moiety.

65. The reporter system component of claim 64 wherein the first putative binding moiety is a protein.

66. The reporter system component of claim 64 wherein the protein is selected from the group consisting of members of a signal transduction cascade, cell surface receptors, proteins regulating apoptosis, proteins that regulate progression of the cell-cycle, proteins involved in the development of tumors, transcriptional-regulatory proteins, translational regulatory proteins, proteins that affect cell interactions, cell adhesion molecules, proteins which are members of ligand-receptor pairs, proteins that participate in the folding of other proteins, and proteins involved in targeting to intracellular compartments.

67. A reporter system comprising the reporter system component of claim 63 and further comprising at least a second low-affinity reporter subunit coupled to a second putative binding partner of the first putative binding moiety.

68. The reporter system of claim 67 wherein the binding affinity of the putative binding moieties for each other is greater than the binding affinity of the first and second reporter subunits for each other.

69. The reporter system of claim 68 wherein the production of the signal is dependent upon the binding of the putative binding moieties.

70. The reporter system of claim 67 wherein the first and second putative binding moieties are proteins.

71. The reporter system of claim 70 wherein the protein is selected from the group consisting of members of a signal transduction cascade, cell surface receptors, proteins regulating apoptosis, proteins that regulate progression of the cell-cycle, proteins involved in the development of tumors, transcriptional-regulatory proteins, translational regulatory proteins, proteins that affect cell interactions, cell adhesion molecules, proteins which are members of ligand-receptor pairs, proteins that participate in the folding of other proteins, and proteins involved in targeting to intracellular compartments.

72. The reporter system of claim 70, wherein the first and second reporter subunits each comprise a protein, and wherein said proteins are capable of associating to catalyze a reaction to produce a detectable signal.

73. The reporter system of claim 72 wherein the associated reporter subunits catalyze a reaction to produce a product which is directly detectable as the detectable signal.

74. The reporter system of claim 70 wherein the first and second subunits are low affinity binding mutant subunits of a hydrolytic enzyme.

75. The reporter system of claim 74 wherein the first and second subunits are low affinity binding mutant subunits of β-galactosidase.

76. The reporter system of claim 70, wherein the first and second subunits are low affinity binding mutant subunits of an enzyme.

77. The reporter system of claim 67 wherein the first putative binding moiety and the second putative binding partner comprise identical molecules.

78. The reporter system component of claim 63 wherein said component comprises a fusion protein including said low affinity reporter subunit and said first putative binding moiety.

79. The reporter system component of claim 78 herein the low affinity reporter subunit comprises a low affinity binding mutant subunit of β-galactosidase.

80. A nucleic acid encoding the fusion protein of claim 78.

81. The nucleic acid of claim 80 further comprising regulatory sequences effecting expression of the putative binding protein.

82. A cell transformed with the nucleic acid of claim 80.

83. The reporter system of claim 63, wherein the detectable signal is amplifiable.

84. A method of determining the occurrence of binding between first and second putative binding moieties, the method comprising:

a) providing a reporter system comprising:
   a first component comprising a first low affinity reporter subunit, coupled to the first putative binding moiety, and
   a second component comprising a second low affinity reporter subunit coupled to the second putative binding moiety;
      wherein the first low affinity reporter subunit associates with at least the second low affinity reporter subunit to generate a detectable signal in situ in a cell, said association being mediated by the binding of the first and second putative binding moieties;

b) combining the first component and the second component; and c) detecting the presence or absence of the signal in situ in a cell.

85. The method of claim 84 wherein the binding affinity of the putative binding moieties for each other is greater than the binding affinity of the first and second reporter subunits for each other.

86. The method of claim 84 wherein the first and second putative binding moieties are proteins.

87. The method of claim 86 wherein the protein is selected from the group consisting of members of a signal transduction cascade, cell surface receptors, proteins regulating apoptosis, proteins that regulate progression of the cell-cycle, proteins involved in the development of tumors, transcriptional-regulatory proteins, translational regulatory proteins, proteins that affect cell interactions, cell adhesion molecules, proteins which are members of ligand-receptor pairs, proteins that participate in the folding of other proteins, and proteins involved in targeting to intracellular compartments.

88. The method of claim 84, wherein the first and second reporter subunits each comprise a protein, and wherein said proteins are capable of associating to catalyze a reaction to produce a detectable signal.

89. The method of claim 88 wherein the associated reporter subunits catalyze a reaction to produce a product which is directly detectable as the detectable signal.

90. The method of claim 89 wherein the first and second subunits are low affinity binding mutant subunits of β-galactosidase.

91. The method of claim 84 wherein each of said first and second components comprises a fusion protein.

92. The method of claim 91 wherein the low affinity reporter subunit comprises a low affinity binding mutant subunit of β-galactosidase.

93. The method of claim 92 wherein step (a) comprises transforming a cell with one or more nucleic acids encoding the fusion proteins.

94. The method of claim 84 wherein the degree of binding is quantitated.

95. The method of claim 84 wherein the method further comprises detecting the effect of a third moiety on the binding of the first and second binding moieties, the method further comprising, after step (a) and prior to step (b), combining said reporter system with said third moiety.

96. The method of claim 84 wherein the intracellular localization of the signal is determined.

97. The method of claim 84 wherein step (b) comprises combining the first and second components in the presence of a substance to determine the effect of the substance on binding of the first and second binding moieties.

98. The method of claim 97 wherein the first and second reporter units, and first and second binding moieties, each are proteins;

wherein the components provided in step (a) each comprise a fusion protein including the reporter subunit and the binding moiety;

wherein step (b) comprises expressing nucleic acid sequences encoding the first and second components within a cell suspected to contain the substance which inhibits or promotes binding of the binding moieties; and wherein step (c) comprises detecting the presence or absence of the signal in the cell, thereby to determine the presence or absence in the cell of the substance which acts as an inhibitor or promoter of binding between the binding moieties.

99. The method of claim 97 wherein the substance is selected from the group consisting of a protein, lipid, carbohydrate, nucleic acid, and a small molecule pharmaceutical.

100. The method of claim 97 wherein the substance is a peptide, drug or synthetic analog.

101. The method of claim 97, wherein the substance directly of indirectly affects an upstream event which results in an effect on binding of the first and second binding moieties.

102. A method of screening for binding of a first binding moiety with members of a plurality of different second putative binding moieties, the method comprising:

a) providing a plurality of reporter systems each comprising:

a first component comprising a first low affinity reporter subunit coupled to the first binding moiety, and one of a plurality of second components each comprising a second low affinity reporter subunit coupled to one of said plurality of second putative binding moieties, wherein in each of said second components, said second putative binding moiety is different;

wherein the first low affinity reporter subunit associates with the second low affinity reporter subunit to generate a detectable signal in situ in a cell upon the binding of the first binding moiety with one of said different second putative binding moieties;

b) individually combining the first component with each of the plurality of second components to produce a plurality of binding assay samples, each of which includes the first component and a different one of the second components; and c) detecting the presence or absence of the signal in situ in a cell in each of the binding assay samples.

103. The method of claim 102 wherein the first and second components each comprise a fusion protein including the binding moiety and the reporter subunit.

104. The method of claim 103 wherein, in step (b), the components are expressed from a nucleic acid sequence introduced into a cell.

105. The method of claim 104, wherein the plurality of second putative binding moieties are encoded by members of a cDNA library.

106. The method of claim 105, wherein the cell is selected from the group consisting of a eukaryotic cell, a mammalian cell, and a human cell.

107. The method of claim 102, wherein, in step (c), the signal is quantitated.

108. The method of claim 102, wherein cells in which binding between the first binding moiety and one of the plurality of putative second binding moieties has occurred are separated from cells in which said binding has not occurred.

109. The method of claim 108, wherein separation is by fluorescence-activated cell sorting.

110. The method of claim 102, wherein the first binding moiety is selected from the group consisting of cell surface receptors, transcriptional regulatory proteins, translational regulatory proteins, replication proteins, splicing proteins, signal transduction proteins, cell-cell adhesion molecules, cell-substrate adhesion molecules, cell-cycle proteins, oncogene products, tumor suppressor proteins, membrane receptors, proteins regulating apoptosis, developmental regulatory proteins, proteins that affect cell interactions, proteins that participate in the folding of other proteins, proteins involved in targeting to intracellular compartments, viral proteins, and cytoskeletal proteins.

111. A method of determining the occurrence of association between first and second moieties, the method comprising:

a) providing a reporter system comprising:

a first component comprising a first low affinity reporter subunit, coupled to the first moiety, and a second component comprising a second low affinity reporter subunit coupled to the second moiety;

wherein the first low affinity reporter subunit associates with at least the second low affinity reporter subunit to generate a detectable signal in situ in a cell, said association being mediated by association between the first and second moieties, wherein association between the first and second moieties is mediated by at least a third moiety;

b) combining the first component, the second component and the third moiety; and c) detecting the presence or absence of the signal in situ in a cell.

* * * * *

UNITED STATES PATENT AND TRADEMARK OFFICE
CERTIFICATE OF CORRECTION

| | | |
|---|---|---|
| PATENT NO. | : 6,342,345 B1 | Page 1 of 1 |
| APPLICATION NO. | : 09/053614 | |
| DATED | : January 29, 2002 | |
| INVENTOR(S) | : Blau et al. | |

It is certified that error appears in the above-identified patent and that said Letters Patent is hereby corrected as shown below:

Replace Column 1, line no. 14-20 with:

-- FEDERALLY-SPONSORED RESEARCH OR DEVELOPMENT
This invention was made with Government support under contracts CA059717 and HD018179 awarded by the National Institutes of Health and under contract DAMD17-00-1-0442 awarded by the Department of the Army. The Government has certain rights in this invention --

Signed and Sealed this
First Day of January, 2013

David J. Kappos
*Director of the United States Patent and Trademark Office*